US012329788B2

(12) United States Patent
Ochrombel et al.

(10) Patent No.: US 12,329,788 B2
(45) Date of Patent: Jun. 17, 2025

(54) SYNBIOTIC COMPOSITIONS

(71) Applicant: Evonik Operations GmbH, Essen (DE)

(72) Inventors: Ines Ochrombel, Essen (DE); Bodo Speckmann, Kahl (DE); Stefan Pelzer, Guetersloh (DE); Michael Schwarm, Alzenau (DE); Walter Pfefferle, Langgoens (DE)

(73) Assignee: Evonik Operations GmbH, Essen (DE)

( * ) Notice: Subject to any disclaimer, the term of this patent is extended or adjusted under 35 U.S.C. 154(b) by 805 days.

(21) Appl. No.: 17/049,155

(22) PCT Filed: Apr. 18, 2019

(86) PCT No.: PCT/EP2019/060158
§ 371 (c)(1),
(2) Date: Oct. 20, 2020

(87) PCT Pub. No.: WO2019/206820
PCT Pub. Date: Oct. 31, 2019

(65) Prior Publication Data
US 2022/0088091 A1 Mar. 24, 2022

(30) Foreign Application Priority Data
Apr. 23, 2018 (EP) .................... 18168783

(51) Int. Cl.
| | |
|---|---|
| *C12N 1/20* | (2006.01) |
| *A23K 10/18* | (2016.01) |
| *A23K 10/30* | (2016.01) |
| *A23K 20/147* | (2016.01) |
| *A23K 20/163* | (2016.01) |
| *A23K 20/174* | (2016.01) |
| *A23K 20/20* | (2016.01) |
| *A23K 40/30* | (2016.01) |
| *A23L 33/00* | (2016.01) |
| *A23L 33/105* | (2016.01) |
| *A23L 33/125* | (2016.01) |
| *A23L 33/135* | (2016.01) |
| *A23L 33/15* | (2016.01) |
| *A23L 33/16* | (2016.01) |
| *A23L 33/175* | (2016.01) |

(Continued)

(52) U.S. Cl.
CPC .......... *A61K 35/742* (2013.01); *A23K 10/18* (2016.05); *A23K 10/30* (2016.05); *A23K 20/147* (2016.05); *A23K 20/163* (2016.05); *A23K 20/174* (2016.05); *A23K 20/30* (2016.05); *A23K 40/30* (2016.05); *A23L 33/105* (2016.08); *A23L 33/125* (2016.08); *A23L 33/135* (2016.08); *A23L 33/15* (2016.08); *A23L 33/16* (2016.08); *A23L 33/175* (2016.08); *A23L 33/18* (2016.08); *A23L 33/40* (2016.08); *A61K 9/48* (2013.01); *A61K 31/05* (2013.01); *A61K 31/07* (2013.01); *A61K 31/122* (2013.01); *A61K 31/197* (2013.01); *A61K 31/198* (2013.01); *A61K 31/355* (2013.01); *A61K 31/375* (2013.01); *A61K 31/4188* (2013.01); *A61K 31/4415* (2013.01); *A61K 31/455* (2013.01); *A61K 31/51* (2013.01); *A61K 31/519* (2013.01); *A61K 31/525* (2013.01); *A61K 31/593* (2013.01); *A61K 31/702* (2013.01); *A61K 31/714* (2013.01); *A61K 31/733* (2013.01); *A61K 33/00* (2013.01); *A61K 33/04* (2013.01); *A61K 33/06* (2013.01); *A61K 33/18* (2013.01); *A61K 33/24* (2013.01); *A61K 33/26* (2013.01); *A61K 33/30* (2013.01); *A61K 33/32* (2013.01); *A61K 33/34* (2013.01); *A61K 35/748* (2013.01); *A61K 36/258* (2013.01); *A61K 36/31* (2013.01); *A61K 36/63* (2013.01); *A61K 36/738* (2013.01); *A61K 36/87* (2013.01); *A61K 36/8962* (2013.01); *A61K 36/9066* (2013.01); *A61K 36/9068* (2013.01); *A61K 38/05* (2013.01); *A23V 2002/00* (2013.01)

(58) Field of Classification Search
None
See application file for complete search history.

(56) References Cited

U.S. PATENT DOCUMENTS

| | | |
|---|---|---|
| 6,429,220 B1 | 8/2002 | Yagi et al. |
| 2012/0251512 A1 | 10/2012 | Farmer et al. |

(Continued)

FOREIGN PATENT DOCUMENTS

| | | |
|---|---|---|
| CN | 104323029 A | 2/2015 |
| CN | 107319105 A | 11/2017 |

(Continued)

OTHER PUBLICATIONS

International Search Report and Written Opinion issued on Jul. 11, 2019 in PCT/EP2019/060158 filed on Apr. 18, 2019.

(Continued)

*Primary Examiner* — Jennifer E Graser
(74) *Attorney, Agent, or Firm* — Oblon, McClelland, Maier & Neustadt, L.L.P.

(57) ABSTRACT

A synbiotic preparation may include at least one probiotic strain and at least one amino acid or derivative thereof selected from glutamine, glutamic acid or salts thereof, conjugated glutamine, or oligopeptides of 2-10 amino acid units in length, wherein the amino acid units may be natural amino acids, and at least one amino acid unit being a glutamine or glutamic acid unit.

15 Claims, 13 Drawing Sheets
Specification includes a Sequence Listing.

(51) Int. Cl.
| | | |
|---|---|---|
| A23L 33/18 | (2016.01) | |
| A61K 9/48 | (2006.01) | |
| A61K 31/05 | (2006.01) | |
| A61K 31/07 | (2006.01) | |
| A61K 31/122 | (2006.01) | |
| A61K 31/197 | (2006.01) | |
| A61K 31/198 | (2006.01) | |
| A61K 31/355 | (2006.01) | |
| A61K 31/375 | (2006.01) | |
| A61K 31/4188 | (2006.01) | |
| A61K 31/4415 | (2006.01) | |
| A61K 31/455 | (2006.01) | |
| A61K 31/51 | (2006.01) | |
| A61K 31/519 | (2006.01) | |
| A61K 31/525 | (2006.01) | |
| A61K 31/593 | (2006.01) | |
| A61K 31/702 | (2006.01) | |
| A61K 31/714 | (2006.01) | |
| A61K 31/733 | (2006.01) | |
| A61K 33/00 | (2006.01) | |
| A61K 33/04 | (2006.01) | |
| A61K 33/06 | (2006.01) | |
| A61K 33/18 | (2006.01) | |
| A61K 33/24 | (2019.01) | |
| A61K 33/26 | (2006.01) | |
| A61K 33/30 | (2006.01) | |
| A61K 33/32 | (2006.01) | |
| A61K 33/34 | (2006.01) | |
| A61K 35/742 | (2015.01) | |
| A61K 35/748 | (2015.01) | |
| A61K 36/258 | (2006.01) | |
| A61K 36/31 | (2006.01) | |
| A61K 36/63 | (2006.01) | |
| A61K 36/738 | (2006.01) | |
| A61K 36/87 | (2006.01) | |
| A61K 36/8962 | (2006.01) | |
| A61K 36/9066 | (2006.01) | |
| A61K 36/9068 | (2006.01) | |
| A61K 38/05 | (2006.01) | |

(56) References Cited

U.S. PATENT DOCUMENTS

| | | |
|---|---|---|
| 2014/0220662 A1 | 8/2014 | Hashman |
| 2015/0017144 A1 | 1/2015 | Herthel et al. |
| 2015/0118203 A1* | 4/2015 | Boyette ............... A61K 35/741 119/51.01 |
| 2016/0362654 A1 | 12/2016 | Hashman et al. |
| 2017/0000755 A1* | 1/2017 | Arhancet ............... A23K 50/10 |
| 2017/0173093 A1 | 6/2017 | Herthel et al. |
| 2017/0189457 A1 | 7/2017 | Farmer et al. |
| 2018/0042972 A1 | 2/2018 | Gould et al. |
| 2019/0046595 A1 | 2/2019 | Herthel et al. |

FOREIGN PATENT DOCUMENTS

| | | |
|---|---|---|
| KR | 20010074950 A1 | 8/2001 |
| KR | 2015-0039816 A1 | 4/2015 |
| WO | 2014/020138 A2 | 2/2014 |
| WO | WO 2014/020226 A1 | 2/2014 |
| WO | 2017/207371 A1 | 12/2017 |
| WO | 2017/207372 A1 | 12/2017 |
| WO | WO 2019/002471 A1 | 1/2019 |
| WO | WO 2019/002476 A1 | 1/2019 |
| WO | WO 2019/038153 A1 | 2/2019 |

OTHER PUBLICATIONS

Russian Office Action issued on Jan. 17, 2023 in Russian Patent Application No. 2020134461/04 (with English translation), 22 pages.

Xie et al., "Optimization of Glutamine Peptide Production from Soybean Meal and Analysis of Molecular Weight Distribution of Hydrolysates", International Journal of Molecular Sciences, 2012, vol. 13, pp. 7483-7495.

Guarner et al., "Probiotics and Prebiotics", World Gastroenterology Organisation (WGO), 2008, Retrieved from the Internet: URL: https://www.worldgastroenterology.org/UserFiles/file/guidelines/probiotics-russian-2008.pdf, pp. 1-24.

* cited by examiner

SEQUENCE LISTING

```
<160> NUMBER OF SEQ ID NOS: 3

<210> SEQ ID NO 1
<211> LENGTH: 19
<212> TYPE: DNA
<213> ORGANISM: Artificial Sequence
<220> FEATURE:
<223> OTHER INFORMATION: Bacterial 16S rRNA gene forward primer

<400> SEQUENCE: 1
cgaaagcgtg gggagcaaa                                                  19

<210> SEQ ID NO 2
```

```
<211> LENGTH: 19
<212> TYPE: DNA
<213> ORGANISM: Artificial Sequence
<220> FEATURE:
<223> OTHER INFORMATION: Bacterial 16S rRNA gene reverse primer

<400> SEQUENCE: 2
gttcgtactc cccaggcgg                                               19

<210> SEQ ID NO 3
<211> LENGTH: 21
<212> TYPE: DNA
<213> ORGANISM: Artificial Sequence
<220> FEATURE:
<223> OTHER INFORMATION: Bacterial 16S rRNA gene probe.  Probe:
      6FAM-ATTAGATACCCTGGTAGTCCA-MGB.
<220> FEATURE:
<221> NAME/KEY: misc_feature
<222> LOCATION: (1)..(1)
<223> OTHER INFORMATION: 6FAM-
<220> FEATURE:
<221> NAME/KEY: misc_feature
<222> LOCATION: (21)..(21)
<223> OTHER INFORMATION: -MGB

<400> SEQUENCE: 3
attagatacc ctggtagtcc a                                            21
```

SYNBIOTIC COMPOSITIONS

REFERENCE TO A SEQUENCE LISTING

In accordance with 37 CFR § 1.52(e)(5), the present specification makes reference to a Sequence Listing (submitted electronically as a .txt file named "532890US_ST25.txt". The .txt file was generated on Nov. 2, 2021 and is 1,055 bytes in size. The entire contents of the Sequence Listing are herein incorporated by reference.

The current invention concerns a synbiotic preparation containing at least one probiotic strain and at least one amino acid or derivative thereof selected from glutamine, glutamic acid or salts thereof, conjugated glutamine, or oligopeptides of 2-10 amino acid units in length, said amino acid units being natural amino acids, and at least one amino acid unit being a glutamine or glutamic acid unit.

The gastrointestinal microbiota modulates health and has therefore emerged as a target of interventions to improve the health of humans and animals. Microbiota-targeted strategies include the application of prebiotics, probiotics, and sometimes even fecal transplantations with the intention to modify the composition and activity of the microbiota. Probiotics are live microorganisms, which confer a health benefit on the host when administered in adequate amounts [1]. The most commonly investigated and commercially available probiotics are mainly microorganisms from species of genera *Lactobacillus* and Bifidobacterium. In addition, several others such as *Propionibacterium, Streptococcus, Bacillus, Enterococcus, Escherichia coli*, and yeasts are also used. Different bacterial strains of the same genus and species may exert different effects on the host.

Per definition, probiotics exert benefits to the host through their activity in the human body, proposed mode of action include normalization of the host's microbiota, inhibition of pathogens, interaction with the immune system, and their own metabolic activity. More specifically, favorable effects on microbiota compositions can include an increase of taxa belonging to the *clostridium* group IV (also known as the *Clostridium leptum* group) and *clostridium* group XIVa (also known as the *Clostridium Coccoides* group), both groups belong to the group of strict extremophile anaerobes, and a decrease of *clostridium* group XI taxa. For instance, the *Clostridium soredelli* group belongs to the cluster XI and causes pneumonia, endocarditis, arthritis, peritonitis and myonecrosis.

The *Clostridium* cluster XIVa includes species belonging to the *Clostridium, Eubacterium, Ruminococus, Coporococcus, Dorea, Lachnospira, Roseburia* and *Butyrivibrio* genera. *Clostridium* cluster IV is composed by the *Clostridium, Eubacterium, Ruminococcus* and *Anaerofilum genera* [2]. The *Clostridium* cluster XI possesses pathogenic species like *Clostridium difficile*. The *Clostridium cluster* XIVa and IV make up a substantial part (10-40%) of the total bacteria in the gut microbiota [3], which is an essential actor in the defense mechanisms and in the resistance to infection.

The functionality of microbiota is described by the production of substances such as organic acids, diacetyl, short chain fatty acids, biosurfactants, gases, modified bile acids, phytochemicals, and antibacterial substances such as bacteriocins and hydrogen peroxide. Among the favorable short-chain fatty acids (SCFA) are in particular acetate and n-butyrate. For instance, acetate improves health by inhibition of enteropathogens.

Addition of some food ingredients to the diet could promote beneficial bacteria. The so-called prebiotics are defined as selectively fermented ingredients that results in specific changes in the composition and/or activity of the gastrointestinal microbiota, thus conferring benefits upon host health. Prebiotics often act as entrapping matrices during the gastrointestinal transit, further releasing the microorganism in the intestine and then serving as fermentable substrates [4]. Most prebiotics are complex carbohydrates from plant origin. Prebiotics and probiotics can be combined to support survival and metabolic activity of the latter and the resulting products belong to the class of synbiotics. Synbiotics refer to food ingredients or dietary supplements combining probiotics and prebiotics in a form of synergism, hence synbiotic [5]. An updated definition of the term prebiotics is: "a substrate that is selectively utilized by host microorganisms conferring a health benefit" [6], thus referring not only to certain carbohydrates but also to e.g. amino acids and peptides.

Food supplements are concentrated sources of nutrients or other substances with a nutritional or physiological effect, whose purpose is to supplement the normal diet (www.efsa.europa.eu/en/topics/topic/food-supplements). For instance, it is described for L-glutamine that oral supplementation alters composition of gut microbiota in overweight humans reducing the Firmicutes to Bacteriodetes ratio, which has also been observed in weight loss programs [7]. Favorable effects on a microbiota's activity can be an increased production of acetate and n-butyrate, and a decreased production of branched-chain short-chain fatty acids, such as iso-butyrate and iso-valerate. N-butyrate can be introduced as a so-called colonic fuel into the lipid biosynthesis, and production of gut hormones. Furthermore, butyric acid is a physiological component of the colonic environment that possesses anti-inflammatory and antitumor properties [8], and it supports many additional functions of the human body to prevent the formation of non-communicable diseases [9, 10]. The reduction of iso-forms of butyrate and valerate indicates decreased protein fermentation in the gut, and a reduction of harmful fermentation products.

Although some probiotics have shown promising results in research studies, strong scientific evidence to support specific uses of probiotics for most health conditions is lacking. The U.S. Food and Drug Administration (FDA) and the European Food Safety Authority (EFSA) have so far not approved any probiotic for preventing or treating health problems. Several probiotic strategies have not been successful, because the microorganisms often show poor survival and colonization in the gastrointestinal tract. Limiting factors include low pH in the stomach, as well as presence of bile and digestive enzymes, low oxygen content, and the presence of other microorganisms in the intestine. In addition, not only the viability but also the maintenance of the metabolic activity of the strains are important for the probiotic functionality [11].

Probiotic treatment can have insufficient impact on dysbiosis in several cases, which is associated with many disorders, and a lack of modulation of gut resident beneficial and pathogenic microbes. Furthermore, there is a lack of availability of some beneficial microbes for the use as supplements (e.g. *Faecalibacterium prausnitzii*, and others). Methods like fecal microbiota transplant (FMT), also known as bacteriotherapy, are complex and include the risk of unintended adverse consequences.

Although reduction of intestinal pathogens has often been proposed to belong to the beneficial effects of prebiotics, this has not been conclusively demonstrated. Like other non-digestible carbohydrates, prebiotics are fermented by gut bacteria and resulting SCFAs are known for their health-promoting properties. In fact, SCFA production is influenced by food intake and gut microbiota composition. These molecules are involved in shaping the gut environment and physiology of the colon as they are energy sources for host cells and intestinal microbiota as well as participating in different host-signaling mechanism [12]. Acetate, propionate and butyrate are abundant SCFA in the gut. Propionate can be incorporated into gluconeogenesis by the synthesis of odd-numbered fatty acids. A precursor for the formation of SCFA is lactate.

Thus, prebiotic strategies mainly include fermentable oligosaccharides, disaccharides, monosaccharides, and polyols (FODMAP) and are aimed at increasing the production of these metabolites as well as the abundance of beneficial microbes. However, these carbohydrates often cause unwanted side-effects, e.g. diarrhea, constipation, and flatulence. A low FODMAP diet effectively reduces these symptoms in patients with irritable bowel syndrome [13].

Conclusively, there is a requirement for strategies that target the gastrointestinal microbiota to induce favorable shifts in their composition and activity to achieve beneficial effects on host health. Such concept should specifically focus on effects on clostridia, because they belong to the leading players in the maintenance of gut homeostasis [14]. These rod-shaped bacteria of the Firmicutes phylum are Gram-positive and make up a substantial part of the total bacteria in the gut microbiota. They start to colonize the intestine of breastfed infants during the first month of life and populate a specific region in the intestinal mucosa in close relationship with intestinal cells. This position allows them to participate as crucial factors in modulating physiologic, metabolic and immune processes in the gut during the entire lifespan, by interacting with the other resident microbe populations, but also by providing specific and essential functions.

Various probiotic strains and their use as feed and food additive have been described before (only exemplary reference is made to WO 2017/207371 A1 and WO 2017/207372 A1). However, for the known probiotic strains no effect on the composition of the gut microbiota has been described before in such detail regarding the specific bacterial strains and their distribution.

Therefore, it was an objective of the present invention to provide new combinations of probiotic strains which show positive effects on the gastrointestinal microbiota by inducing favorable shifts in their composition, especially related to clostridia and promoting production of the favorable SCFA, such as acetate and n-butyrate in the gastrointestinal tract.

A subject of the present invention is therefore a synbiotic preparation comprising at least one probiotic strain selected from *Bacillus subtilis, Bacillus licheniformis, Bacillus amyloliquefaciens* and *Bacillus pumilus*, and at least one amino acid selected from glutamine, glutamic acid or salts thereof, conjugated glutamine, or oligopeptides of 2-10 amino acid units in length, said amino acid units being natural amino acids, and at least one amino acid unit being a glutamine or glutamic acid unit.

FIG. 1A-J shows pie charts showing at genus level of i-screen fermentation samples based on MiSeq sequencing of the V4 hypervariable region of the 16S rRNA encoding region gene.

Figure 8:
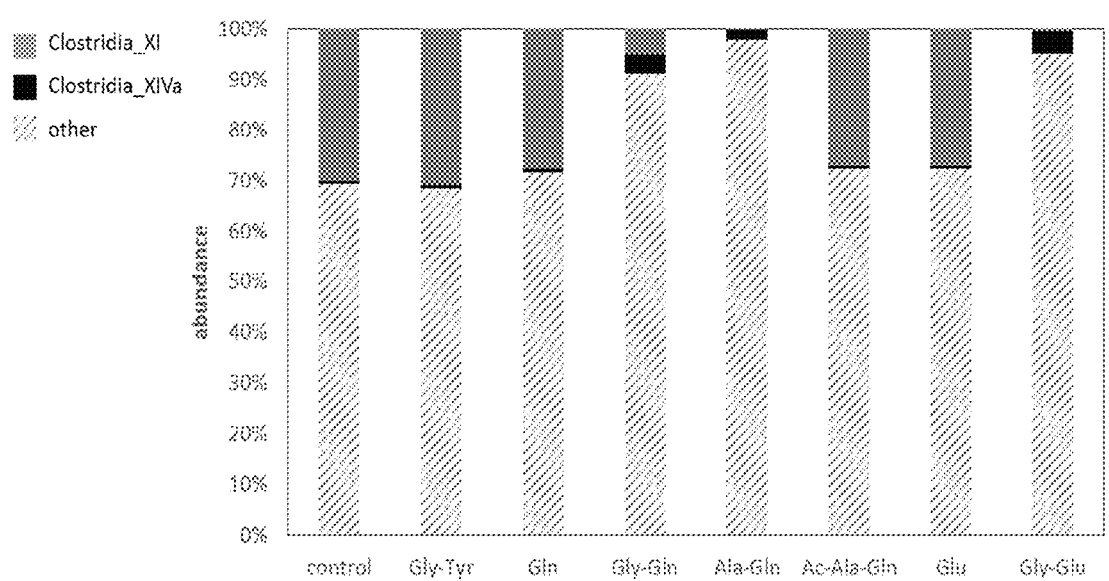
Figure 9:
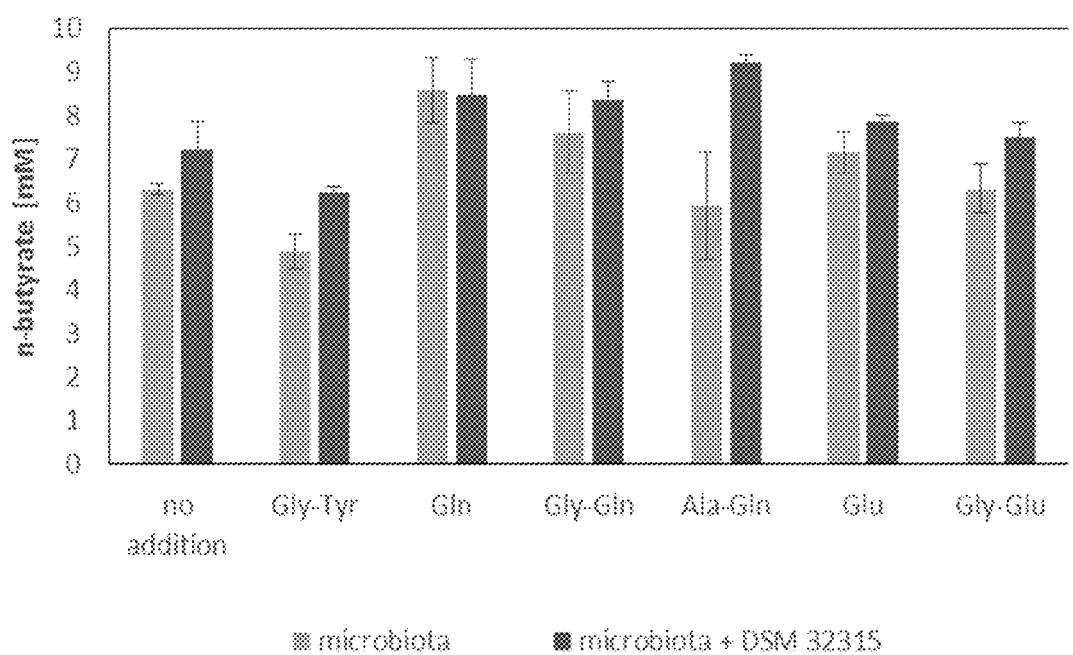

FIG. 8 shows bar graph showing at genus level of i-screen fermentation samples based on MiSeg sequencing of the V4 hypervariable region of the 16S rRNA encoding region gene, FIG. 9 shows after 24 h incubation in SIEM with human microbiota measured n-butyrate concentrations in mM in the presence of colon microbiota containing different amino acids, or dipeptides with and without the combination of *B. subtilis* DSM 32315 cells.

Figure 10:
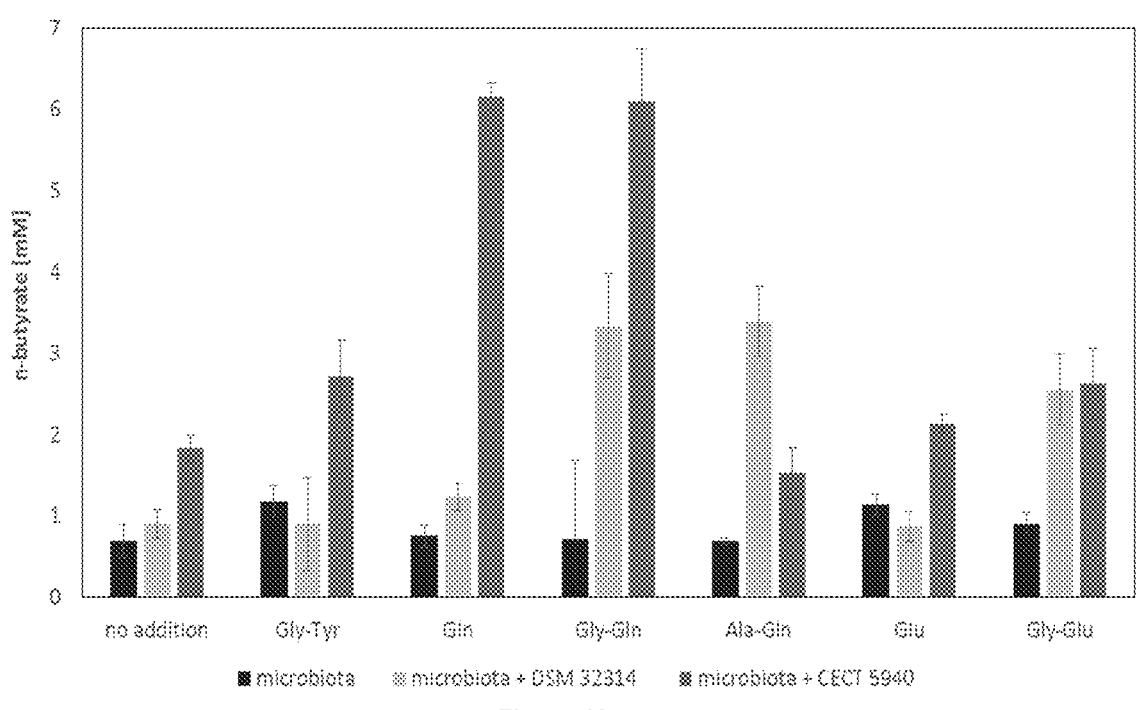

FIG. 10 shows after 24 h incubation in SIEM with human microbiota measured n-butyrate concentrations in mM in the presence of colon microbiota containing different amino acids, or dipeptides with and without the combination of *B. licheniformis* (DSM 32314) or *B. amyloliquefaciens* (CECT 5940) cells.

This new synbiotic preparation containing a bacterial strain and glutamine or derivatives of glutamine promotes n-butyrate-producing taxa and increased levels of n-butyrate in the intestine.

Bacteria of the genus *Bacillus* were found to be especially suitable for this effect. Therefore, in a preferred configuration of the present invention the probiotic strain comprises a bacterial strain of the genus *Bacillus*. In particular, bacterial strains from the species *Bacillus subtilis, Bacillus licheniformis* and *Bacillus amyloliquefaciens* effectively increase the proportion of *clostridium* group XIVa members, and at the same time reduce *clostridium* group XI taxa in the intestine. This effect is accompanied by increased lactate, acetate and n-butyrate, but decreased iso-butyrate and iso-valerate levels at the same time. Surprisingly, it was found that L-glutamine and glutamic acid and derivatives thereof strongly induce *clostridium* group XIVa and inhibit *clostridium* group XI taxa. Like for the effect of *Bacillus subtilis*, this microbiota effect was linked to an increase of acetate and n-butyrate, and a decrease of iso-butyrate and iso-valerate. The increase of acetate and n-butyrate levels can be explained by a glutamic acid fermentation pathway that is used by certain Clostridia [15]. Moreover, combinations of *Bacillus subtilis* strains with glutamine or derivatives thereof act synergistically and exert stronger effects on clostridial clusters and production of short-chain fatty acids than the single components. The usage of a *Bacillus* strain as probiotic and/or synbiotic food supplement has the additional advantage of a possible application of heat and acid resistant spores, which is not possible for e.g. non-spore-forming lactobacilli.

It is a big advantage of probiotics in comparison to antibiotics, that they do not destroy bacteria indiscriminately nor do they lead to antibiotic resistant strains of pathogenic bacteria. Normally they are able to selectively compete with pathogenic bacteria by production of antimicrobial substances with specific efficacy, and are ideally able to simultaneously enhance the growth and viability of beneficial gut microflora. Further, they are preferably able to stimulate a systemic immune response in the treated animals or human beings.

In a preferred embodiment the probiotic strain is selected from one of the following: *Bacillus subtilis* DSM 32315 (which is described in detail in WO 2017/207372 A1), *Bacillus subtilis* DSM 32540, and *Bacillus amyloliquefaciens* CECT 5940, *Bacillus subtilis* DSM 32592, *Bacillus pumilus* DSM 32539, *Bacillus licheniformis* DSM 32314 (which is described in detail in WO 2017/207371 A1).

*Bacillus subtilis* DSM 32315 is described by accession number DSM 32315 at the DSMZ Patent Depository, Inhoffenstraβe 7B. 38124 Braunschweig Science Campus Braunschweig-Süd GERMANY. *Bacillus subtilis* DSM 32540 is described by accession number DSM 32540 at the DSMZ Patent Depository, Inhoffenstraβe 7B, 38124 Braunschweig Science Campus Braunschweig-Süd GERMANY. *Bacillus amyloliquefaciens* CECT 5940 is described by accession number CECT 5940 at Colección Española de Cultivos Tipo, 46100 Universidad de Valencia Campus de Burjassot Valencia SPAIN. *Bacillus subtilis* DSM 32592 is described by accession number DSM 32592 at the DSMZ Patent Depository, Inhoffenstraβe 7B, 38124 Braunschweig Science Campus Braunschweig-Süd GERMANY. *Bacillus licheniformis* DSM 32314 is described by accession number DSM 32314 at the DSMZ Patent Depository, Inhoffenstraβe 7B. 38124 Braunschweig Science Campus Braunschweig-Süd GERMANY.

According to the present invention the amino acid or derivative thereof is selected from glutamine, glutamic acid or salts thereof, conjugated glutamine, or oligopeptides of 2-10 amino acid units in length, said amino acid units being natural amino acids, and at least one amino acid unit being a glutamine or glutamic acid unit.

The positive effects of glutamine are known from the literature, for example it has been shown that oral supplementation with glutamine reduced mortality in guinea-pigs treated with doses of methotrexate which induced necrotizing enterocolitis [16]. Moreover, it has been shown in hind-limb balance studies in post-operative anaesthetized dogs that the amino acids of infused alanylglutamine are extracted by skeletal muscle almost as well as from mixtures of alanine and glutamine [17].

An "amino acid", in the context of the present invention, shall be understood as being a molecule comprising an amino functional group (—NH2) and a carboxylic acid functional group (—COOH), along with a side-chain specific to the respective amino acid. In the context of the present invention, both alpha- and beta-amino acids are included. Preferred amino acids of the invention are alpha-amino acids, in particular the 20 "natural amino" acids as follows:

| | |
|---|---|
| Alanine | (Ala/A) |
| Arginine | (Arg/R) |

-continued

| | |
|---|---|
| Asparagine | (Asn/N) |
| Aspartic acid | (Asp/D) |
| Cysteine | (Cys/C) |
| Glutamic acid | (Glu/E) |
| Glutamine | (Gln/Q) |
| Glycine | (Gly/G) |
| Histidine | (His/H) |
| Isoleucine | (Ile/I) |
| Leucine | (Leu/L) |
| Lysine | (Lys/K) |
| Methionine | (Met/M) |
| Phenylalanine | (Phe/F) |
| Proline | (Pro/P) |
| Serine | (Ser/S) |
| Threonine | (Thr/T) |
| Tryptophan | (Trp/W) |
| Tyrosine | (Tyr/Y) |
| Valine | (Val/V) |

In the context of the present invention, the expression "natural amino acids" shall be understood to include both the L-form and the D-form of the above listed 20 amino acids. The L-form, however, is preferred. In one embodiment, the term "amino acid" also includes analogues or derivatives of those amino acids.

A "free amino acid", according to the invention, is understood as being an amino acid having its amino and its (alpha-) carboxylic functional group in free form, i.e., not covalently bound to other molecules, e.g., an amino acid not forming a peptide bond. Free amino acids may also be present as salts or in hydrate form. When referring to an amino acid as a part of, or in, an oligopeptide, this shall be understood as referring to that part of the respective oligopeptide structure derived from the respective amino acid, according to the known mechanisms of biochemistry and peptide biosynthesis.

An "oligopeptide", according to the invention, shall be understood as being a peptide compound consisting of 2 to 20 amino acids. More preferred oligopeptides of the inventions are oligopeptides consisting of 2-10 amino acids, 2-6 amino acids, 2-5 amino acids, 2-4 amino acids, or 2-3 amino acids. Most preferred oligopeptides according to the invention are dipeptides.

The preference of smaller peptides is consistent with the early literature, which shows that studies in young animals have suggested that dipeptide transport is of greater quantitative significance than free amino acid transport during early growth [18, 19]. Moreover, in human intestinal perfusion studies di- and tripeptide uptake was inhibited less than free amino acid uptake following 2 weeks of starvation [20].

A "peptide" shall be understood as being a molecule comprising at least two amino acids covalently coupled to each other by a peptide bond (R1-CO—NH—R2).

In an alternative embodiment of the present invention the oligopeptide further contains alanine or glycine.

In a further alternative embodiment, the oligopeptide is a dipeptide selected from Glycine-Glutamine, Glycine-Glutamic acid, Alanine-Glutamine, Alanine-Glutamic acid and its acetylated forms.

The Dipeptide Alanine-Glutamine (Ala-Gln) is particularly preferred according to a preferred embodiment of the present invention.

According to the present invention, the total amount of probiotic strain and amino acid or oligopeptide is at least 40 weight-%, preferably at least 50 weight-% more preferably at least 60 weight-%, most preferably at least 70 weight-% of the total weight of the preparation.

It is particularly preferred, when the preparation further comprises an enteric coating according to the present invention, to directly deliver the symbiotic composition to the colon of the individual. The enteric coating composition may comprise one or more of the following: methyl acrylate-methacrylic acid copolymers, cellulose acetate phthalate (CAP), cellulose acetate succinate, Hydroxypropyl methyl cellulose phthalate, hydroxypropyl methyl cellulose acetate succinate (hypromellose acetate succinate), polyvinyl acetate phthalate (PVAP), methyl methacrylate-methacrylic acid copolymers, shellac, cellulose acetate trimellitate, sodium alginate, zein.

As an enteric coating it is preferred to use a polymer polymerized from 10 to 30% by weight methyl methacrylate, 50 to 70% by weight methyl acrylate and 5 to 15% by weight methacrylic acid.

The polymer dispersion as disclosed may preferably comprise 15 to 50% by weight of a polymer polymerized from 20 to 30% by weight methyl methacrylate, 60 to 70% by weight methyl acrylate and 8 to 12% by weight methacrylic acid. Most preferred the polymer is polymerized from 25% by weight methyl methacrylate, 65% by weight methyl acrylate and 10% by weight methacrylic acid.

A 30% by weight aqueous dispersion of a polymer polymerized from 25% by weight methyl methacrylate, 65% by weight methyl acrylate and 10% by weight methacrylic acid corresponds to the commercial product EUDRAGUARD® biotic.

The percentages of the monomers add up to 100%. The functional polymer is applied in amounts of 2-30 mg/cm$^2$, preferably 5-20 mg/cm$^2$.

One subject of the present invention is the use of a preparation according to the present invention as a feed or food supplement.

A further subject of the current invention is also the use of a preparation of the current invention as a synbiotic ingredient in feed or food products. According to the present invention, the term "synbiotic" shall refer to a composition comprising a prebiotic and a probiotic component. Moreover, the invention refers to the updated definition of the term "prebiotic", meaning a substrate that is selectively utilized by microorganisms and conferring a health benefit and shall also include amino acids and peptides. A symbiotic composition according to the present invention is therefore a composition comprising a probiotic strain and an amino acid or oligopeptide as prebiotic.

Preferred foodstuffs according to the invention are dairy products, in particular yoghurt, cheese, milk, butter and quark.

The cells of the strains of the current invention may be present, in particular in the compositions of the current invention, as spores (which are dormant), as vegetative cells (which are growing), as transition state cells (which are transitioning from growth phase to sporulation phase) or as a combination of at least two, in particular all of these types of cells. In a preferred embodiment, the composition of the current invention comprises mainly or only spores.

A further subject of the present invention is a feed- or foodstuff composition containing a preparation according to the present invention and at least one further feed or food ingredient, preferably selected from proteins, carbohydrates, fats, further probiotics, prebiotics, enzymes, vitamins, immune modulators, milk replacers, minerals, amino acids, coccidiostats, acid-based products, medicines, and combinations thereof.

The feed- or foodstuff composition according to the present invention does also include dietary supplements in the form of a pill, capsule, tablet or liquid.

The compositions of the present invention, in particular the feed, food and pharmaceutical compositions, preferably comprise the strains of the current invention and are administered to animals or human beings at a rate of about $1 \times 10^3$ to about $2 \times 10^{12}$ CFU/g feed/food or ml water, in particular in a rate of about $1 \times 10^3$ or about $1 \times 10^4$ or about $1 \times 10^5$ or about $1 \times 10^6$ or about $1 \times 10^7$ or about $1 \times 10^8$ or about $1 \times 10^9$ or about $1 \times 10^{10}$ or about $1 \times 10^{11}$ or about $1 \times 10^{12}$ CFU/g feed/food or ml water, preferably in an amount of about $1 \times 10^4$ to about $1 \times 10^{10}$ CFU/g feed/food or ml water, more preferably in an amount of $1 \times 10^4$ to $1 \times 10^7$ CFU/g feed/food or ml water.

Correspondingly, preferred amounts of the preparations of the current invention in the feed or food compositions of the current invention range preferably from 0.1 wt.-% to 10 wt.-%, more preferably from 0.2 wt.-% to 5 wt.-%, in particular from 0.3 wt.-% to 3 wt.-%.

A further subject of the current invention is a pharmaceutical composition containing a preparation according to the present invention and a pharmaceutically acceptable carrier.

The preparations according to the present invention, when administered to animals or human beings, preferably improve the health status, in particular gut health, cardiovascular health, healthy weight management or immune health of an animal or a human being.

A further subject of the current invention is therefore a composition according to the present invention for use in the prevention or treatment of diarrhea, constipation, irritable bowel syndrome, Crohn's disease, ulcerative colitis, colorectal cancer, bowel cancer, cardiovascular disease, arteriosclerosis, fatty liver disease, hyperlipidemia, hypercholesterolemia, obesity, adipositas, type 2 diabetes, metabolic syndrome, chronic inflammatory diseases, and allergic diseases.

An advantageous configuration according to the present invention is a composition for improving the gut health status of an animal or a human being by one or more of the following:
  increasing the total amount of bacteria of the *Clostridium* group XIVa in the gut microbiome,
  reducing the total amount of bacteria of the *Clostridium* group XI in the gut microbiome,
  increasing production of short chain fatty acids, preferably n-butyrate, propionate, acetate and lactate, and
  inhibiting formation of branched-chain short-chain fatty acids, preferably iso-butyrate and iso-valerate.

A further subject of the present invention is a capsule comprising at least one probiotic strain selected from *Bacillus subtilis, Bacillus licheniformis, Bacillus amyloliquefaciens, Bacillus pumilus* and at least one dipeptide selected from Glycine-Glutamine, Glycine-Glutamic acid, Alanine-Glutamine, Alanine-Glutamic acid and its acetylated forms.

In a preferred embodiment, the probiotic strain is *Bacillus subtilis*, preferably *Bacillus subtilis* DSM 32315, *Bacillus subtilis* DSM 32540, *Bacillus subtilis* DSM 32592.

The capsule preferably comprises between $1 \times 10^8$ and $2 \times 10^{20}$ CFU of the probiotic strain and between 50 mg and 800 mg of the dipeptide.

It is also preferred, when the amount of probiotic strain and dipeptide is at least 40 weight-%, preferably at least 50 weight-% more preferably at least 60 weight-%, most preferably at least 70 weight-% of the total weight of the capsule filling.

The capsule may further contain additional vitamins or minerals. The vitamins are preferably selected from vitamin A (as all-trans-retinol, all-trans-retinyl-esters, as well as all-trans-beta-carotene and other provitamin A carotenoids), vitamin B1 (thiamine), vitamin B2 (riboflavin), vitamin B3 (niacin), vitamin B5 (pantothenic acid), vitamin B6 (pyridoxine), vitamin B7 (biotin), vitamin B9 (folic acid or folate), vitamin B12 (cobalamins), vitamin C (ascorbic acid), vitamin D (calciferols), vitamin E (tocopherols and tocotrienols) and vitamin K (quinones).

The minerals are preferably selected from sulfur, iron, chlorine, calcium, chromium, cobalt, copper, zinc, magnesium, manganese, molybdenum, iodine and selenium.

The capsule may further comprise one or more prebiotic ingredients, preferably selected from inulins, fructooligosaccharides (FOS), galactooligosaccharides (GOS), starch, pectin, beta-glucans and xylooligosaccharides.

The capsule may further comprise one or more plant extracts, wherein the plants are preferably selected from broccoli, olive fruit, pomegranate, blackcurrant, blueberry, bilberry, sea buckthorn, camu camu, boysenberry, curcuma, ginger, garlic, grape seeds, acai berry, aronia, goji berry, horseradish, boswellia serrata, spirulina, panax ginseng, cannabidiol, rose hip, pu erh, sencha, echinacea and green tea leaves.

In a preferred configuration, the capsule comprises an enteric coating, wherein the enteric coating comprises one or more of the following: methyl acrylate-methacrylic acid copolymers, cellulose acetate phthalate (CAP), cellulose acetate succinate, Hydroxypropyl methyl cellulose phthalate, hydroxypropyl methyl cellulose acetate succinate (hypromellose acetate succinate), polyvinyl acetate phthalate (PVAP), methyl methacrylate-methacrylic acid copolymers, shellac, cellulose acetate trimellitate, sodium alginate, zein.

WORKING EXAMPLES

Example 1: Strains *Bacillus subtilis* DSM 32315, *Bacillus subtilis* DSM 32540, *Bacillus licheniformis* DSM 32314 and *Bacillus amyloliquefaciens* CECT 5940 are Able to Persist in the Colonic Human Microbiota Intestinal Screening Model To determine the effect of the probiotic strains *Bacillus subtilis* DSM 32315, *Bacillus subtilis* DSM 32540, *Bacillus licheniformis* DSM 32314 and *Bacillus amyloliquefaciens* CECT 5940 on adult colonic microbiota, an intestinal screening model was used (i-screen, TNO, the Netherlands). Therefore the i-screen model was inoculated with standard human adult fecal microbiota material, which consisted of pooled fecal donations from 6 healthy adult volunteers (Caucasian, European lifestyle and nutrition). The fecal material was mixed and grown in a fed-batch fermenter for 40 hours to create a standardized microbiota as described previously [21]. These standard adult gut microbiota sets were stored at −80° C. in 12% glycerol.

The intestinal microbiota was cultured in vitro in modified standard ileal efflux medium (SIEM), the composition of which was described by [22] and modified as follows: 0.047 g/l pectin, 0.047 g/l xylan, 0.047 g/l arabinogalactan, 0.047 g/l amylopectin, 0.392 g/l starch, 24.0 g/l casein, 24.0 Bacto pepton, 0.4 ox-bile and 0.2 g/l cysteine. All components were supplied by Trititium Microbiology (Veldhoven, The Netherlands). The pH of the medium was adjusted to 5.8. For the i-screen fermentations, the precultured standardized fecal inoculum was diluted 50 times in 1350 µl modified SIEM. All experiments have been carried out in triplicates. The strains *Bacillus subtilis* (DSM 32315), *Bacillus subtilis* DSM 32540, *Bacillus licheniformis* DSM 32314 and *Bacillus amyloliquefaciens* CECT 5940 were precultured separately in 50 ml LBKelly medium [23], for about 16 h. Incubation was done in shaking flasks at 37° C. under aerobic conditions. After incubation, bacterial density was determined by optical density measurement at 600 nm. A final stock solution of $1\times10^{10}$ cells/ml was prepared in 1 ml buffer solution (0.1 mM MES pH 6). The suspension of each strain was introduced into the i-screen to a final level of about $10^9$ cells/ml, respectively The i-screen incubation was performed under following gas conditions: 0.2% $O_2$, 0.2% $CO_2$, 10% $H_2$, 89.6% $N_2$.

DNA Isolation

DNA extraction for the sequencing of 16S rRNA coding genes was performed as described by Ladirat et al. (2013) with some minor modifications. Approximately 100 µl of the culture materials were added to the wells of a 96 well plate containing per well 300 µl of lysis buffer (Mag Mini DNA Isolation Kit, LGC ltd, UK), 500 µl zirconium beads (0.1 mm; BioSpec products, Bartlesville, OK, USA) and 500 µl of phenol saturated with Tris-HCI (pH 8.0; Carl Roth GMBH, Germany). The 96 well plate was placed in a Mini-BeadBeater-96 (BioSpec products, Bartlesville, Okla, USA) for 2 min at 2100 oscillations/min. DNA was subsequently purified using the Agowa Mag Mini DNA Isolation Kit according to the manufacturer recommendations. Extracted DNA was eluted in a final volume of 60 µl buffer.

V4 16S rRNA Gene Sequencing

The microbiota composition was analyzed by 16S rRNA gene amplicon sequencing of the V4 Hypervariable Region. This was Achieved Through a Series of Steps:

The amount of bacterial DNA in the i-screen DNA samples was determined by quantitative polymerase chain reaction (qPCR) using primers specific for the bacterial 16S rRNA gene:

```
Forward primer:
                                         SEQ ID NO. 1
CGAAAGCGTGGGGAGCAAA;

Reverse primer:
                                         SEQ ID NO. 2
GTTCGTACTCCCCAGGCGG;

Probe:
                                         SEQ ID NO. 3
6FAM-ATTAGATACCCTGGTAGTCCA-MGB.
```

Subsequently, PCR amplicons of the V4 hypervariable region of the 16S rRNA gene were generated for the individual samples by amplification of 500 µg of DNA as described by [24] (2013), using F515/R806 primers [25]. Primers included Illumina adapters and a unique 8-nt sample index sequence key [24]. A mock control was included for technical quality control. The amount of amplified DNA per sample was quantified using the dsDNA 910 Reagent Kit on the Fragment Analyzer (Advanced Analytical). The amplicon libraries were pooled in equimolar amounts and purified from 1,2% agarose gel using the Gel Extraction Kit (Qiagen). The Library was quantified using the Quant-iT™ PicoGreen® dsDNA Assay Kit (Thermo Fisher Scientific). Paired-end sequencing of amplicons was conducted on the Illumina MiSeq platform (Illumina, Eindhoven, The Netherlands).

The sequence data was processed with Mothur v.1.36.1 [26] in line with the mothur MiSeq SOP [24]. Before merging the read pairs, low quality regions were trimmed using Btrim [27] with a sliding window size of 5 nt and average quality score of 25. After merging, the sequences were filtered by length while no ambiguous bases were allowed. The unique sequences were aligned to the bacterial SILVA SEED reference alignment release 102 (available at: http://www.mothur.org/wiki/Silva_reference_files); too short sequences were removed using screen. seqs with parameters "optimize=start-end, criteria=90". Chimeric sequences were identified per sample using UCHIME [28] in de novo mode and removed. Next, sequences occurring less than 10 times in the entire dataset were removed. Taxonomic names were assigned to all sequences using the Ribosomal Database Project (RDP) naïBayesian classifier with confidence threshold of 60% and 1000 iterations [29] and the mothur-formatted version of the RDP training set v.9 (trainset9_032012).

Sequences were grouped using Minimum Entropy Decomposition (MED) algorithm that clusters 16S rRNA gene amplicons in a sensitive manner [30]. To filter noise, the "minimum substantive abundance" filter was set to 200.

The colonic human microbiota in the i-screen was also supplemented with viable vegetative *Bacillus* spp. cells of each probiotic strain.

Based on MiSeq sequencing of the V4 hypervariable region of the 16S rRNA encoding gene specific effects on the microbiota composition related to the individual strains could be visualized.

Based on the number of sequence reads, the abundance of bacilli was high at start of the i-screen experiment (about $10^9$ cfu/ml), and thus *Bacillus subtilis* DSM 32315 contributed to approximately 91% of the total bacterial population at t=0 h (FIG. 1 C), *Bacillus subtilis* DSM 32540 contributed to approximately 87% of the total bacterial population at t=0 h (FIG. 1 E), *Bacillus licheniformis* DSM 32314 contributed to approximately 94% of the total bacterial population at t=0 h (FIG. 1 G) and *Bacillus amyloliquefaciens* CECT 5940 contributed to approximately 88% of the total bacterial population at t=0 h (FIG. 1 I).

The control without added *Bacillus* spp. strain is shown at time point 0 h (FIG. 1 A) and after 24 h of incubation (FIG. 1 B). Upon 24 h incubation, the fecal microbiota was able to recover on the expense of the relative presence of the bacilli. It appeared that the DSM 32315 cells were persistent being present at a level of 41% in i-screen after 24 h incubation (FIG. 1 D), the DSM 32540 cells were persistent being present at a level of 19% in i-screen after 24 h incubation (FIG. 1 F), the DSM 32314 cells were persistent being present at a level of 4% in i-screen after 24 h incubation (FIG. 1 H) and the CECT 5940 cells were persistent being present at a level of 7% in i-screen after 24 h incubation (FIG. 1 J).

FIG. 1 shows pie Charts showing at genus level of i-screen fermentation samples based on MiSeq sequencing of the V4 hypervariable region of the 16S rRNA encoding region gene. The detected genera and their relative abundance are represented by shaded sections. A) 0 h incubation without any addition B) after 24 h incubation without any addition C) 0 h after addition of vegetative *Bacillus subtilis* DSM 32315 cells D) 24 h after addition of vegetative *Bacillus subtilis* DSM 32315 cells E) 0 h after addition of vegetative *Bacillus subtilis* DSM 32540 cells F) 24 h after addition of vegetative *Bacillus subtilis* DSM 32540 cells G) 0 h after addition of vegetative *Bacillus licheniformis* DSM 32314 cells H) 24 h after addition of vegetative *Bacillus licheniformis* DSM 32314 cells I) 0 h after addition of vegetative *Bacillus amyloliquefaciens* CECT 5940 cells J) 24 h after addition of vegetative *Bacillus amyloliquefaciens* CECT 5940 cells.

Figure 1A:
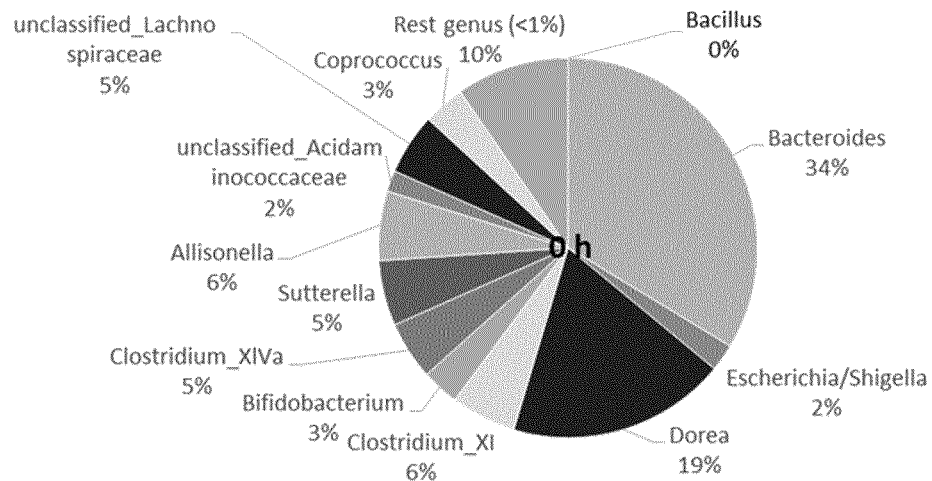
Figure 1B:
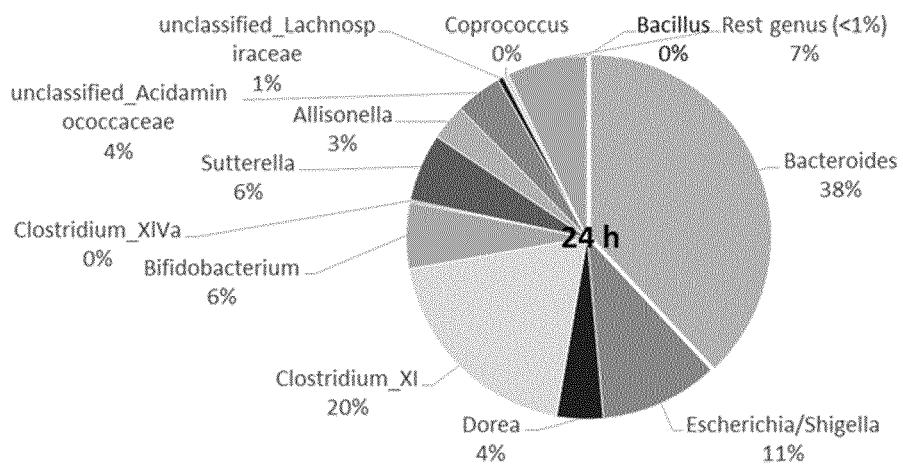
Figure 1C:
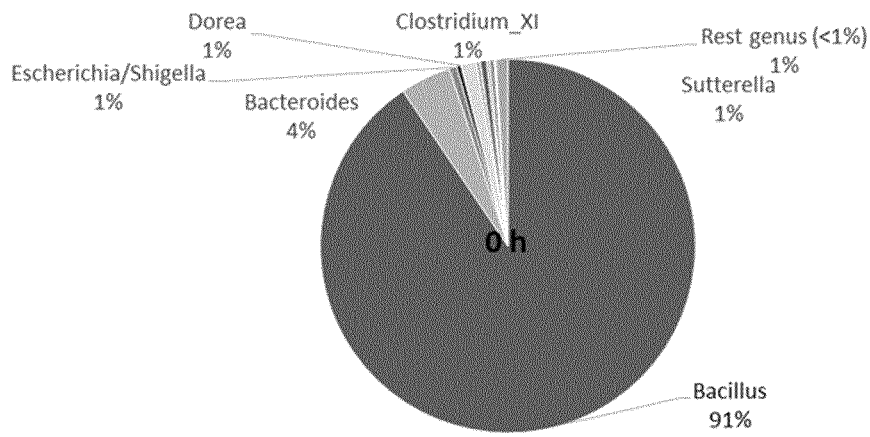
Figure 1D:
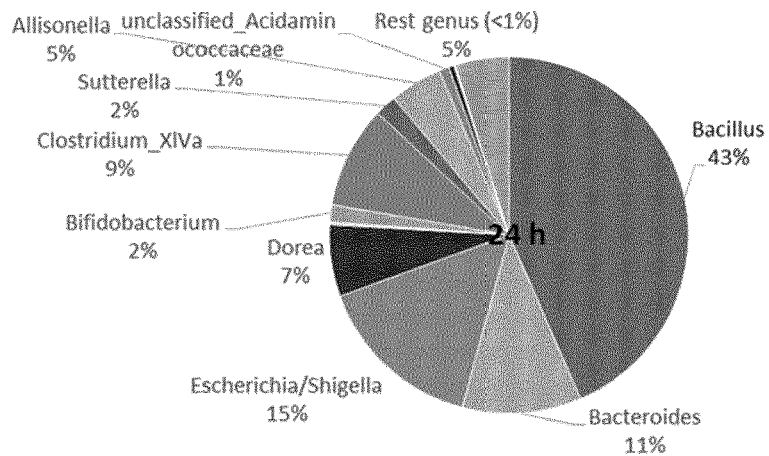
Figure 1E:
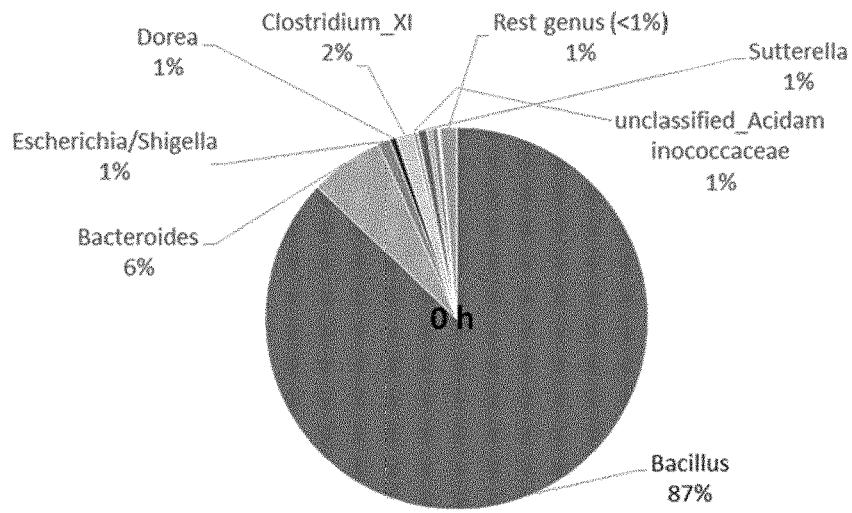
Figure 1F:
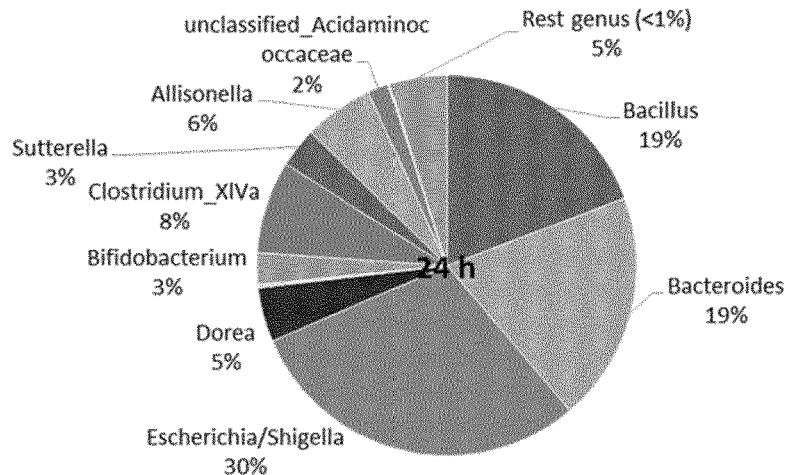
Figure 1G:
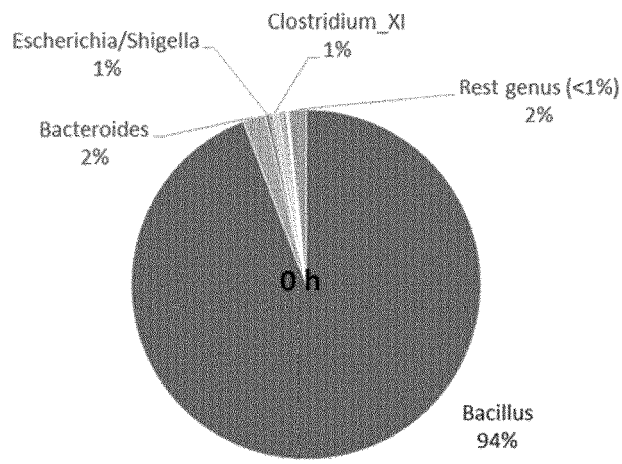
Figure 1H:
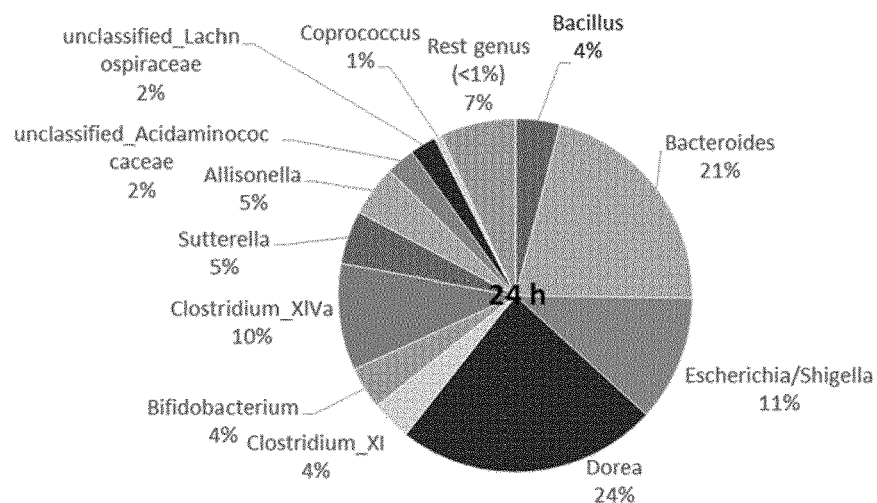
Figure 1I:
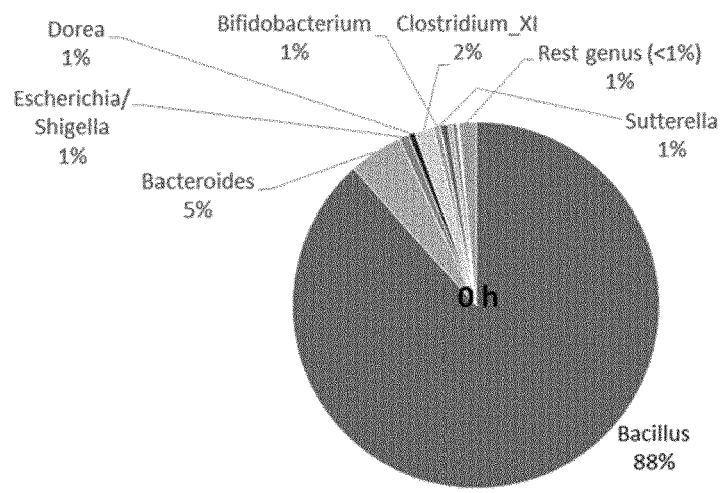
Figure 1J:
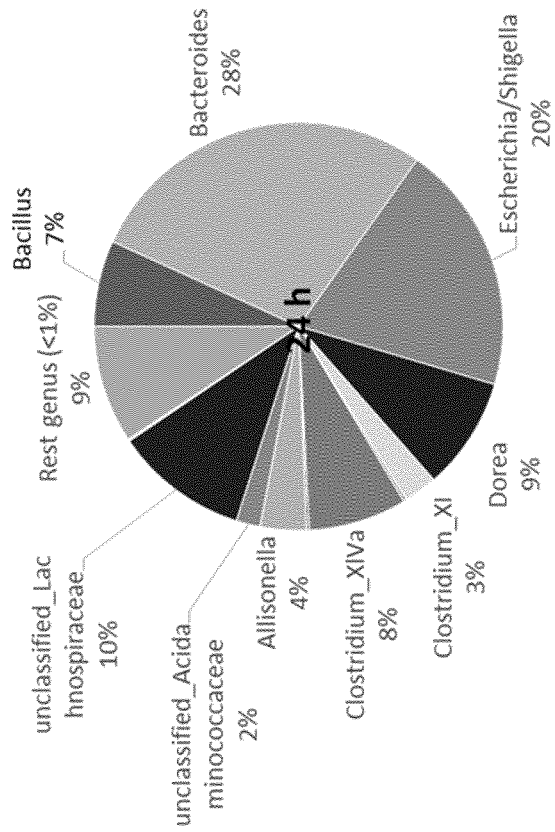
Figure 2:
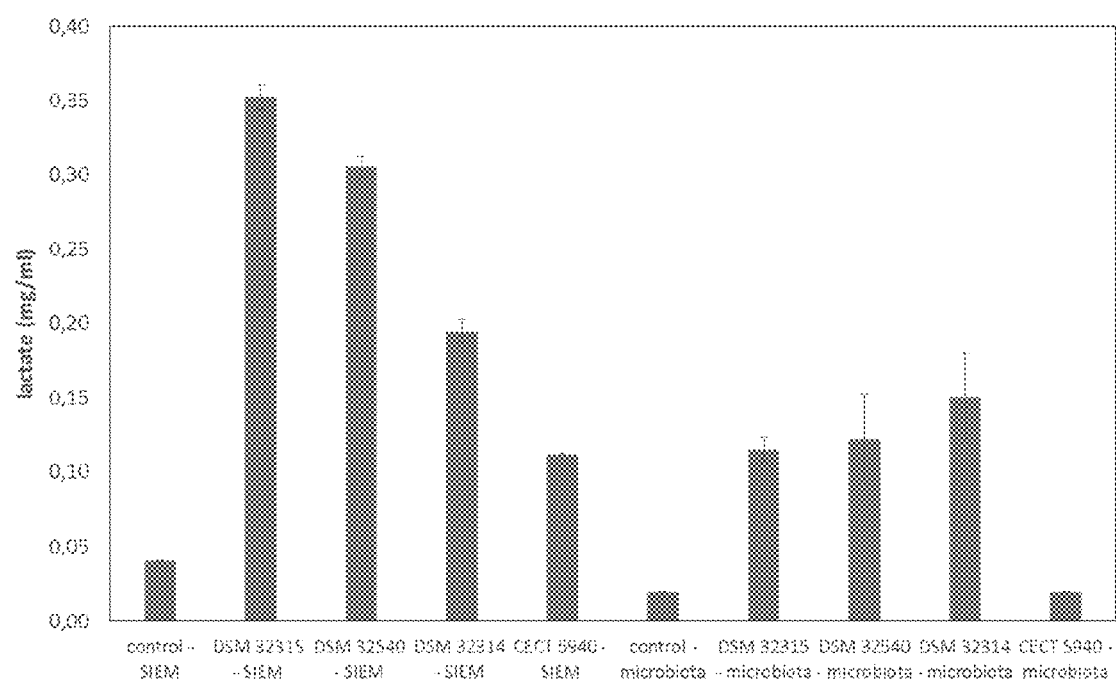
FIG. 2 shows after 24 h incubation in SIEM measured lactate concentrations in mg/ml in SIEM and in the presence of colon microbiota containing *Bacillus subtilis* DSM 32315, *Bacillus subtilis* DSM 32540, *Bacillus licheniformis* DSM 32314 and *Bacillus amyloliquefaciens* CECT 5940.

Example 2: Probiotic Strains *Bacillus subtilis* DSM 32315, *Bacillus subtilis* DSM 32540, *Bacillus licheniformis* DSM 32314 and *Bacillus amyloliquefaciens* CECT 5940 Produce Significant Levels of Lactate In the SIEM at start, a low level of lactate was detected at about 0.04 mg/ml, which fully disappeared in the presence of microbiota with a content of <0.02 mg/ml lactate after 24 h (FIG. 2). The *Bacillus* strains produced significant levels of lactate in the SIEM without colon community after 24 h. The cells of DSM 32315 produced 0.35 mg/ml, the cells of DSM 32540 produced 0.31 mg/ml, the cells of DSM 32314 produced 0.19 mg/ml, and the cells of CECT 5940 produced 0.11 mg/ml.

After 24 h incubation with human gut microbiota the amount of lactate was still significantly increased to 0.12 mg/ml in the presence of DSM 32315 or DSM 32540 cells and to 0.15 g/ml in the presence of DSM 32314, respectively.

Thus, these probiotic strains give rise to a significant lactate formation by the human gut microbiota. This can be interpreted as a beneficial effect, because lactate can be transformed into health promoting SCFAs.

FIG. 2 shows after 24 h incubation in SIEM measured lactate concentrations in mg/ml in SIEM and in the presence of colon microbiota containing *Bacillus subtilis* DSM 32315, *Bacillus subtilis* DSM 32540, *Bacillus licheniformis* DSM 32314 and *Bacillus amyloliquefaciens* CECT 5940, respectively. Limit detection of lactate was 0.02 mg/ml.

Figure 3:
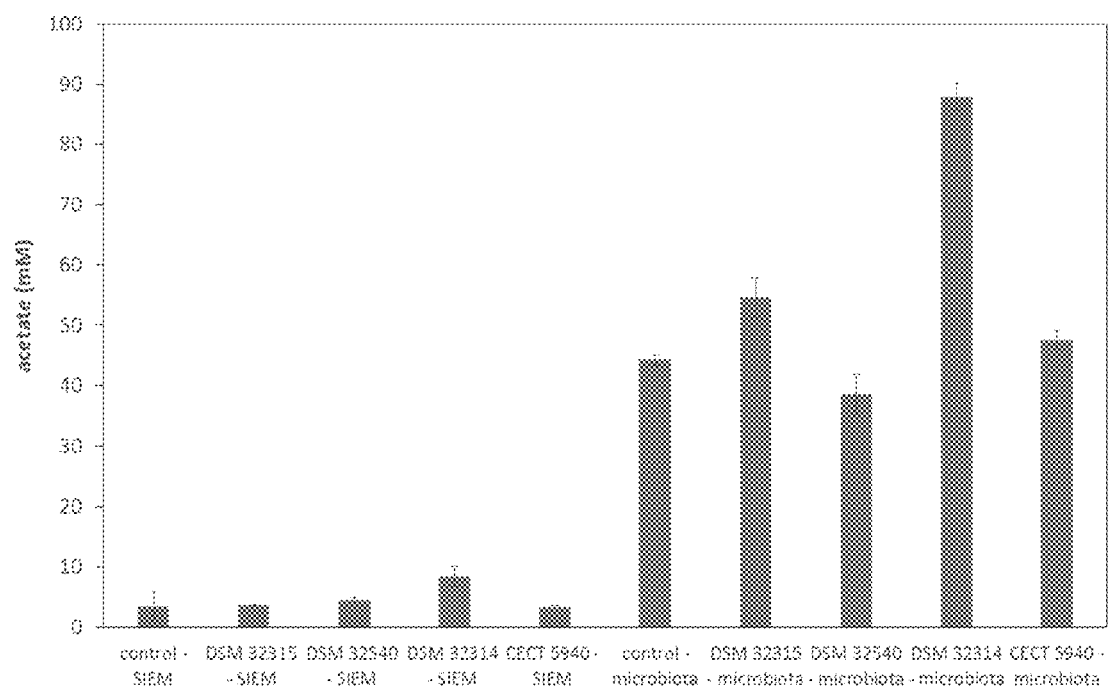
FIG. 3 shows after 24 h incubation in SIEM measured acetate concentrations in mM in SIEM and in the presence of colon microbiota containing *Bacillus subtilis* DSM 32315, *Bacillus licheniformis* DSM 32314 and *Bacillus amyloliquefaciens* CECT 5940.

Example 3: Probiotic Strains *Bacillus subtilis* DSM 32315, *Bacillus licheniformis* DSM 32314 and *Bacillus amyloliquefaciens* CECT 5940 Support Acetate Production by the Human Microbiota Community, Respectively The *Bacillus* strains DSM 32315, DSM 32314 and CECT 5940 cause a substantial increase in the acetate production of the gut microbiota. FIG. 3 shows an average acetate level of about 44 mM in the i-screen after 24 h exposure without added probiotic strains, while acetate is with 3.4 mM in the SIEM hardly detectable.

After 24 h incubation increases of 10.4 mM, 43.7 mM and 3.3 mM in acetate concentrations are observed in the presence of the strains DSM 32315, DSM 32314 and CECT 5940, respectively (FIG. 3).

The p-value for all data are below 0.05, which means they are statistically significant. Thus, the probiotic strains DSM 32315, DSM 32314 and CECT 5940 supports acetate production, which has a beneficial effect on the human gut.

FIG. 3 shows after 24 h incubation in SIEM measured acetate concentrations in mM in SIEM and in the presence of colon microbiota containing *Bacillus subtilis* DSM 32315, *Bacillus licheniformis* DSM 32314 and *Bacillus amyloliquefaciens* CECT 5940, respectively.

Figure 4:
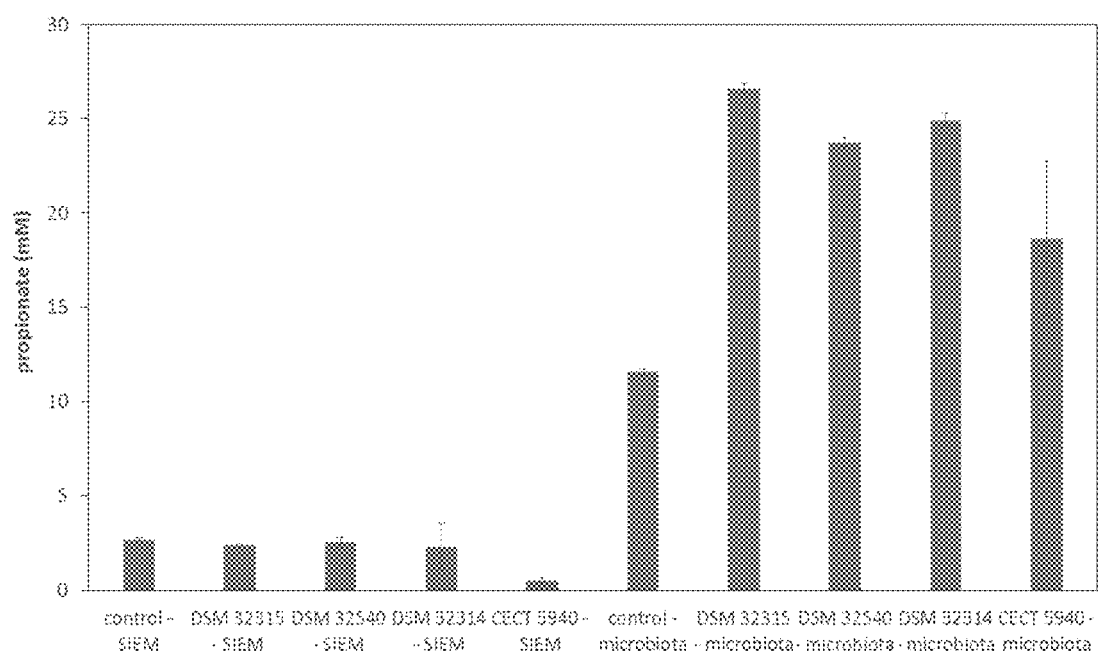
FIG. 4 shows after 24 h incubation in SIEM measured propionate concentrations in mM in SIEM and in the presence of colon microbiota containing *Bacillus subtilis* DSM 32315. *Bacillus subtilis* DSM 32540, *Bacillus licheniformis* DSM 32314 and *Bacillus amyloliquefaciens* CECT 5940.

Example 4: Probiotic Strains *Bacillus subtilis* DSM 32315, *Bacillus subtilis* DSM 32540, *Bacillus licheniformis* DSM 32314 and *Bacillus amyloliquefaciens* CECT 5940 Support the Production of Propionate by the Human Microbiota, Respectively The *Bacillus* strains DSM 32315, DSM 32540, DSM 32314 and CECT 5940 do not produce propionate in SIEM, but they significantly (p-value<0.05) accelerate propionate production by human microbiota (FIG. 4). The strains support significantly the production of propionate by the gut microbiota compared to the control. FIG. 4 shows an average propionate level of about 11.5 mM in the i-screen after 24 h exposure without added probiotic strains, while propionate is with 2.7 mM hardly detectable in the SIEM. In the presence of vegetative *Bacillus subtilis* DSM 32315 cells the amount of propionate was 15.1 mM higher than in the control after 24 h. In the presence of vegetative *Bacillus subtilis* DSM 32540 the propionate amount was 12.2 mM higher. In the presence of DSM 32314 the amount was 13.4 mM higher, and in the presence of CECT 5940 the amount of propionate was 7.1 mM higher.

Propionate is beneficial for the health status of the human gut, because it can be incorporated into gluconeogenesis.

FIG. 4 shows after 24 h incubation in SIEM measured propionate concentrations in mM in SIEM and in the presence of colon microbiota containing *Bacillus subtilis* DSM 32315, *Bacillus subtilis* DSM 32540, *Bacillus licheniformis* DSM 32314 and *Bacillus amyloliquefaciens* CECT 5940, respectively.

Figure 5:
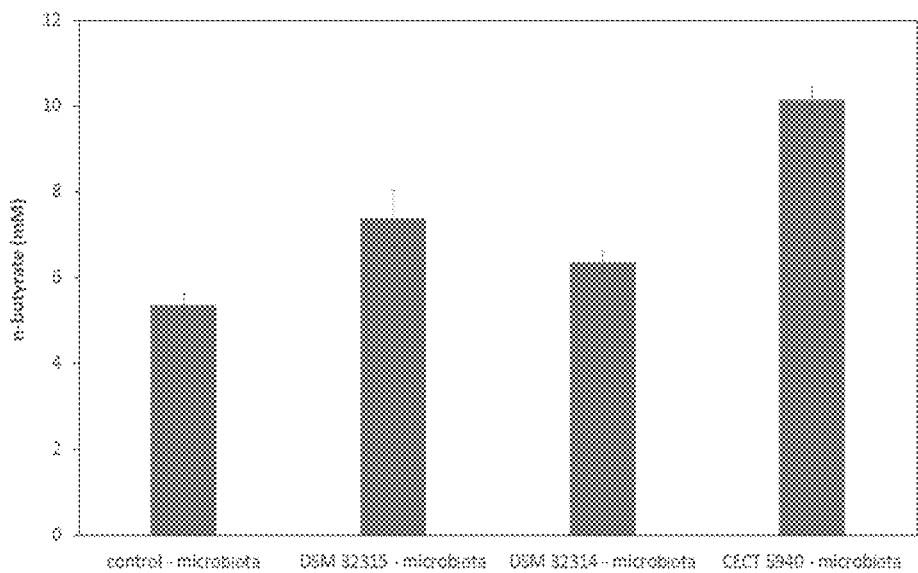
FIG. 5 shows after 24 h incubation in SIEM measured n-butyrate concentrations in mM in the presence of colon microbiota containing *Bacillus subtilis* DSM 32315. *Bacillus licheniformis* DSM 32314 and *Bacillus amyloliquefaciens* CECT 5940.

Example 5: Probiotic Strains *Bacillus subtilis* DSM 32315, *Bacillus licheniformis* DSM 32314 and *Bacillus amyloliquefaciens* CECT 5940 Support the Production of n-Butyrate in a Human Microbiota Composition, Respectively The probiotic strains *Bacillus subtilis* DSM 32315, *Bacillus licheniformis* DSM 32314 and *Bacillus amyloliquefaciens* CECT 5940 do not produce detectable levels of n-butyrate after exposure in SIEM for 24 h, but they have significant positive influences (p-values<0.05) on the level of n-butyrate production by the human microbiota (FIG. 5). FIG. 5 shows an average n-butyrate level of about 5.4 mM in the i-screen after 24 h exposure without added probiotic strains, while propionate is hardly detectable in the SIEM with 0.3 mM. In the presence of vegetative *Bacillus subtilis* DSM 32315 cells the amount of n-butyrate was 2.0 mM higher than in the control after 24 h. In the presence of vegetative cells of DSM 32314 the n-butyrate amount was 1.0 mM higher, and in the presence of vegetative cells of CECT 5940 the n-butyrate amount was 4.8 mM higher. The generation of higher n-butyrate amounts can be beneficial for the lipid biosynthesis, e.g. the production gut hormones.

FIG. 5 shows after 24 h incubation in SIEM measured n-butyrate concentrations in mM in the presence of colon microbiota containing *Bacillus subtilis* DSM 32315, *Bacillus licheniformis* DSM 32314 and *Bacillus amyloliquefaciens* CECT 5940, respectively.

Figure 6:
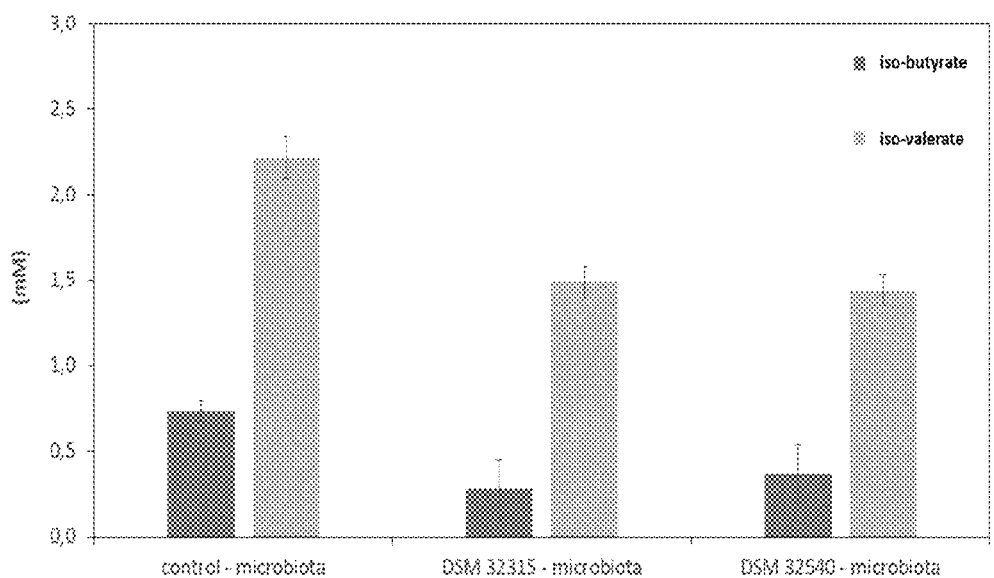
FIG. 6 shows after 24 h incubation in SIEM measured iso-butyrate, and iso-valerate concentrations in mM in the presence of colon microbiota containing *Bacillus subtilis* DSM 32315, and *Bacillus subtilis* DSM 32540.

Example 6: The Strains *Bacillus subtilis* DSM 32315 and DSM 32540 Reduce the Iso-Butyrate and Iso-Valerate Formation in a Human Microbiota Composition, Respectively FIG. 6 shows an average iso-butyrate level of about 0.73 mM and an average iso-valerate level of about 2.2 mM in the i-screen after 24 h exposure without probiotic strains added, while iso-butyrate was not detectable and the content of iso-valerate was 0.24 mM in the SIEM.

In particular, the strains DSM 32315 and DSM 32540 significantly reduce (p-value<0.05) the iso-butyrate and iso-valerate production by the human gut microbiota. After 24 h incubation, the iso-butyrate content was 0.5 mM lower in the presence of cells of DSM 32315 and 0.4 mM lower in the presence of cells of DSM 32540 compared to the control, respectively.

The *Bacillus* strains DSM 32315 and DSM 32540 also have negative influence on the level of iso-valerate production when added to the human microbiota. The concentration is significantly (p-value<0.05) decreased in the i-screen by a value of 0.7 mM and 0.8 mM compared to the control, respectively.

Upon introduction of the *Bacillus* strains DSM 32315 in the gut microbiota in the i-screen the cells support production of n-butyrate and inhibit the formation of iso-butyrate and iso-valerate. This can be an indication of lowered protein fermentation process in the gut, which also indicates a reduced production of harmful by-products.

FIG. 6 shows after 24 h incubation in SIEM measured iso-butyrate, and iso-valerate concentrations in mM in the presence of colon microbiota containing *Bacillus subtilis* DSM 32315, and *Bacillus subtilis* DSM 32540, respectively.

Figure 7:
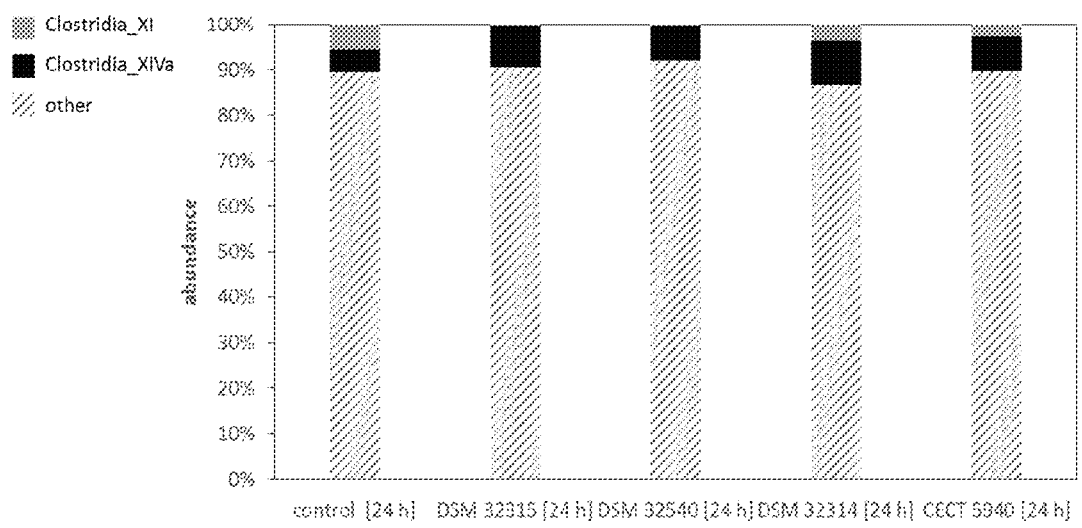
FIG. 7 shows bar graph showing at genus level of i-screen fermentation samples based on MiSeg sequencing of the V4 hypervariable region of the 16S rRNA encoding region gene.

Example 7: Presence of *Bacillus subtilis* DSM 32315, *Bacillus subtilis* DSM 32540, *Bacillus licheniformis* DSM 32314 and *Bacillus amyloliouefaciens* CECT 5940 Reduce Abundance of *Clostridium* XI Cluster, Respectively. The Strains DSM 32315, DSM 32314 and CECT 5940 Increase Abundance of *Clostridium* XIVa Cluster, Respectively When compared to the control at starting time point 0 h (FIG. 1) and the development of the microbiota after 24 h, the presence of strains DSM 32315, DSM 32540, DSM 32314 and CECT 5940 reduces the *Clostridium* XI cluster from 6% down to values below 3% of the total microbial community (FIG. 7). The *Clostridium* XIVa cluster was increased after 24 h from 5% in the control up to at least 8% of the total community in the presence of the probiotic cells, respectively. The i-screen incubation was performed under following gas conditions: 0.2% $O_2$, 0.2% $CO_2$, 10% $H_2$, 89.6% $N_2$.

Thus, in the presence of these probiotic strains the human microbiota composition is shifted to a more healthy community.

FIG. 7 shows bar graph showing at genus level of i-screen fermentation samples based on MiSeq sequencing of the V4 hypervariable region of the 16S rRNA encoding region gene. Shaded bars represent the detected genera *Clostridium* XI and *Clostridium* XIVa and their relative abundance.

Example 8: Addition of Glutamine or Derivates Thereof Changes the Human Microbial Community Significantly The presence of glutamine- or glutamic acid-containing dipeptides influences the microbial community by a shift to an eradicated *Clostridium* group XI and an increased *Clostridium* group XIVa (FIG. 8). The single amino acids were added to a concentration of 3.5 mM and the dipeptides to a concentration of 7 mM. The i-screen exposure was performed as described in example 1 under following gas conditions: 0% $O_2$, 0.2% $CO_2$, 10% Hz, 90% $N_2$. Moreover, Ala-Gln and Gly-Glu reduced the Clostridia XI group almost completely, which is linked to strong beneficial effects on gut health. As controls the dipeptide Gly-Tyr not containing any glutamine or glutamic acid, and the single amino acids glutamine (Gln) and glutamate (Glu) were tested, which had no positive effect on the microbial community.

FIG. 8 shows bar graph showing at genus level of i-screen fermentation samples based on MiSeq sequencing of the V4 hypervariable region of the 16S rRNA encoding region gene. Shaded bars represent the detected genera *Clostridium* XI and *Clostridium* XIVa and their relative abundance.

Example 9: The Combined Addition of *Bacillus subtilis* (DSM 32315), *Bacillus licheniformis* (DSM 32314) or *Bacillus amyloliouefaciens* (CECT 5940) with Glutamine or Derivates Thereof Show Synergistic Effects on Changes Microbial Community and their Short Chain Acid Production than the Single Components The effect of the combination of different probiotic strains together with several glutamine- and glutamic acid containing peptides was analyzed in detail by the method described in example 7. As controls, the effects of glutamine (Gln), glutamic acid (Glu), and the non-Glu/non-Gln dipeptide glycine-tyrosine (Gly-Tyr) alone and in combination with the probiotic strains were analyzed. The single amino acids were added to a concentration of 3.5 mM and the dipeptides to a concentration of 7 mM.

The microbiota composition was analyzed after 24 h incubation. Synergistic positive effects of several combinations on the microbial community composition were observerd, as revealed by a higher increase of percentage of the *Clostridium* XIVa group and a higher decrease of the *Clostridium* group XI compared to the single addition of amino acid or dipeptide and probiotic cells. This synergistic effect was observed for the combination of *B. subtilis* (DSM 32315) with Ala-Gln, Gly-Glu, and Gly-Gln, for *B. licheniformis* (DSM 32314) with Ala-Gln, Gly-Glu, and Gly-Gln, and for *B. amyloliquefaciens* (CECT 5940) with Ala-Gln, Gln, Gly-Glu, and Gly-Gln (table 1).

Thus, in the presence of these probiotic strains in combination with glutamine- or glutamic acid containing dipeptides the human microbiota composition is shifted to a more healthy community.

Example 10: The Combined Addition of *B. subtilis* (DSM 32315), *B. licheniformis* (DSM 32314) or *B. amyloliquefaciens* (CECT 5940) with Glutamine, or Glutamine- or Glutamic Acid-Containing Dipeptides Show Synergistic Effects on the n-Butyrate Production of the Microbial Community The effect of the combination of different probiotic strains together with glutamine, or glutamine- or glutamic acid-containing dipeptides containing peptides on the n-butyrate production of the microbial community was analyzed for the strain *B. subtilis* (DSM 32315) as described in example 1 and 5. The single amino acids were added to a concentration of 3.5 mM and the dipeptides to a concentration of 7 mM.

The n-butyrate content was analyzed after 24 h incubation. Synergistic positive effects on the n-butyrate concentration were observed for the combinations of *B. subtilis* (DSM 32315) with Gln, Gly-Gln, Ala-Gln, Glu, or Gly-Glu, (FIG. 9). This shows that this probiotic strain in combination with glutamine, or glutamic acid, or glutamine-containing peptides have an accelerating effect on the beneficial n-butyrate production of the microbial community. As a negative control the dipeptide Gly-Tyr not containing any glutamine or glutamic acid was tested, which had no positive effect on the n-butyrate production.

FIG. 9 shows after 24 h incubation in SIEM with human microbiota measured n-butyrate concentrations in mM in the presence of colon microbiota containing different amino acids, or dipeptides with and without the combination of *B. subtilis* DSM 32315 cells, respectively.

Example 11: The Combined Addition of *B. licheniformis* (DSM 32314) or *B. amyloliquefaciens* (CECT 5940) Cells with Glutamine, Glutamine- or Glutamic Acid-Containing Dipeptides Show Synergistic Effects on the n-Butyrate Production of the Microbial Community The effects of the combination of different probiotic strains together with glutamine, or glutamine- or glutamic acid-containing dipeptides containing peptides on the n-butyrate production of the microbial community were analyzed

TABLE 1

After 24 h incubation of human microbiota in SIEM with added amino acids, dipeptides and, or probiotic cells (*B. subillis* DSM 32315, *B. licheniformis* DSM 32314, or *B. amyloliquefaciens* CECT 5940) detected genera Clostridium XI, Clostridium XIVa, and others and their relative abundance.

|  | added substrate | control | Gly-Tyr | Gln | Glyn-Gln | Ala-Gln | Ac-Ala-Gln | Glu | Gly-Glu |
|---|---|---|---|---|---|---|---|---|---|
| microbiota | Clostridium_XI | 30% | 31% | 28% | 5% | 0% | 27% | 27% | 0% |
|  | Clostridium_XIVa | 1% | 1% | 1% | 4% | 2% | 1% | 1% | 4% |
|  | other | 69% | 68% | 72% | 91% | 98% | 72% | 72% | 95% |
| microbiota + DSM 32315 | Clostridium_XI | 30% | 33% | 24% | 4% | 0% | 31% | 25% | 0% |
|  | Clostridium_XIVa | 2% | 1% | 2% | 6% | 4% | 2% | 3% | 8% |
|  | other | 68% | 66% | 74% | 90% | 96% | 67% | 72% | 92% |
| microbiota + CECT 5940 | Clostridium_XI | 23% | 28% | 20% | 2% | 0% | 21% | 26% | 0% |
|  | Clostridium_XIVa | 1% | 1% | 1% | 11% | 10% | 1% | 1% | 9% |
|  | other | 76% | 67% | 79% | 88% | 90% | 78% | 73% | 91% |
| microbiota + CECT 5940 | Clostridium_XI | 26% | 28% | 21% | 4% | 0% | 20% | 18% | 0% |
|  | Clostridium_XIVa | 1% | 3% | 9% | 15% | 6% | 4% | 1% | 10% |
|  | other | 72% | 70% | 70% | 81% | 94% | 76% | 80% | 90% | for the strains *B. licheniformis* (DSM 32314) and *B. amyloliquefaciens* (CECT 5940) as described in example 1, 5, and 10. The single amino acids were added to a concentration of 3.5 mM and the dipeptides to a concentration of 7 mM.

The n-butyrate content was analyzed after 24 h incubation. Synergistic positive effects on the n-butyrate concentration were observed for the combinations of *B. licheniformis* (DSM 32314) with Gly-Gln, Ala-Gln, and Gly-Glu (FIG. 10). As well as for the combinations of *B. amyloliquefaciens* (CECT 5940) with Gln, and Gly-Gln.

This shows that this probiotic strain in combination with glutamine, or glutamic acid, or glutamine-containing peptides have an accelerating effect on the beneficial n-butyrate production of the microbial community. As a negative control the dipeptide Gly-Tyr not containing any glutamine or glutamic acid was tested, which had no positive effect on the n-butyrate production.

FIG. 10 shows after 24 h incubation in SIEM with human microbiota measured n-butyrate concentrations in mM in the presence of colon microbiota containing different amino acids, or dipeptides with and without the combination of *B. licheniformis* (DSM 32314) or *B. amyloliquefaciens* (CECT 5940) cells, respectively.

Example 12: Capsules Comprising a *Bacillus subtilis* and Dipeptides as a Prebiotic The following components were filled in HPMC capsules (size 3).

TABLE 2

Preparations for filling into HPMC capsules

| Compound | Capsule I | Capsule II | Capsule III |
|---|---|---|---|
| *Bacillus subtilis* B21 | 66 mg (2 × $10^9$ CFU) | 10 mg (1 × $10^8$ CFU) | 300 mg (2 × $10^{10}$ CFU) |
| Dipeptide Ala-Gln | 400 mg | 50 mg | 800 mg |
| Vitamin B12 | 0.0125 mg | 0.0125 mg | 0.0125 mg |
| Vitamin B6 | 0.7 mg | 0.7 mg | 0.7 mg |
| Zinc | 5 mg | 5 mg | 5 mg |
| Biotin | 25 mg | 25 mg | 25 mg |

The capsules may further contain further prebiotic ingredients, selected from inulins, fructooligosaccharides (FOS), galactooligosaccharides (GOS), starch, pectin, beta-glucans and xylooligosaccharides.

The capsules may further contain one or more plant extracts, selected from broccoli, olive fruit, pomegranate, blackcurrant, blueberry, bilberry, sea buckthorn, camu camu, boysenberry, curcuma, ginger, garlic, grape seeds, acai berry, aronia, goji berry, horseradish, boswellia serrata, spirulina, panax ginseng, cannabidiol, rose hip, pu erh, sencha, echinacea, green tea leaves.

The capsules may comprise further vitamins selected from vitamin A, vitamin B1 (thiamine), vitamin B2 (riboflavin), vitamin B3 (niacin), vitamin B5 (pantothenic acid), vitamin B9 (folic acid or folate), vitamin C (ascorbic acid), vitamin D (calciferols), vitamin E (tocopherols and tocotrienols) and vitamin K (quinones) or minerals selected from sulfur, iron, chlorine, calcium, chromium, cobalt, copper, magnesium, manganese, molybdenum, iodine, and selenium.

Example 13: Capsules Comprising a *Bacillus subtilis* and Dipeptides as a Prebiotic and an Enteric Coating The capsules as prepared in example 12 were coated with an enteric coating composition.

TABLE 3

Coating composition

| Compound | Dry substance [g] | Content based on coating [%] | Weight gain [%] | Content based on capsule [%] |
|---|---|---|---|---|
| EUDRAGUARD ® biotic | 40.8 | 36.9 | 8.2 | 6.7 |
| HPMC | 43.1 | 39.0 | 8.6 | 7.1 |
| Talc | 20.4 | 18.4 | 4.0 | 3.3 |
| Polyethylene glycol | 4.3 | 3.9 | 0.9 | 0.7 |
| Triethyl citrate | 2.0 | 1.8 | 0.4 | 0.3 |

REFERENCES

1. Hill C, Guarner F, Reid G, Gibson G R, Merenstein D J, Pot B, Morelli L, Canani R B, Flint H J, Salminen S et al: Expert consensus document. The International Scientific Association for Probiotics and Prebiotics consensus statement on the scope and appropriate use of the term probiotic. *Nat Rev Gastroenterol Hepatol* 2014, 11(8): 506-514.
2. Collins M D, Lawson P A, Willems A, Cordoba J J, Fernandez-Garayzabal J, Garcia P, Cai J, Hippe H, Farrow J A: The phylogeny of the genus *Clostridium*: proposal of five new genera and eleven new species combinations. *Int J Syst Bacteriol* 1994, 44(4):812-826.
3. Hold G L, Pryde S E, Russell V J, Furrie E, Flint H J: Assessment of microbial diversity in human colonic samples by 16S rDNA sequence analysis. *FEMS Microbiol Ecol* 2002, 39(1):33-39.
4. Koh J H, Choi S H, Park S W, Choi N J, Kim Y, Kim S H: Synbiotic impact of tagatose on viability of *Lactobacillus rhamnosus* strain GG mediated by the phosphotransferase system (PTS). *Food Microbiol* 2013, 36(1):7-13.
5. Pandey K R, Naik S R, Vakil B V: Probiotics, prebiotics and synbiotics—a review. *J Food Sci Technol* 2015, 52(12):7577-7587.
6. Gibson G R, Hutkins R, Sanders M E, Prescott S L, Reimer R A, Salminen S J, Scott K, Stanton C, Swanson K S, Cani P D et al: Expert consensus document: The International Scientific Association for Probiotics and Prebiotics (ISAPP) consensus statement on the definition and scope of prebiotics. *Nat Rev Gastroenterol Hepatol* 2017, 14(8):491-502.
7. de Souza A Z, Zambom A Z, Abboud K Y, Reis S K, Tannihao F, Guadagnini D, Saad M J, Prada P O: Oral supplementation with L-glutamine alters gut microbiota of obese and overweight adults: A pilot study. *Nutrition* 2015, 31(6):884-889.
8. Celasco G, Moro L, Aiello C, Mangano K, Milasi A, Quattrocchi C, R DIM: Calcium butyrate: Anti-inflammatory effect on experimental colitis in rats and antitumor properties. *Biomed Rep* 2014, 2(4):559-563.
9. Riviere A, Selak M, Lantin D, Leroy F, De Vuyst L: Bifidobacteria and Butyrate-Producing Colon Bacteria: Importance and Strategies for Their Stimulation in the Human Gut. *Front Microbiol* 2016, 7:979.
10. Vital M, Karch A, Pieper D H: Colonic Butyrate-Producing Communities in Humans: an Overview Using Omics Data. *mSystems* 2017, 2(6).
11. Gueimonde M, Sanchez B: Enhancing probiotic stability in industrial processes. *Microb Ecol Health Dis* 2012, 23.
12. Rios-Covian D, Ruas-Madiedo P, Margolies A, Gueimonde M, de Los Reyes-Gavilan C G, Salazar N: Intestinal Short Chain Fatty Acids and their Link with Diet and Human Health. *Front Microbiol* 2016, 7:185.
13. Halmos T, Suba I: [Physiological patterns of intestinal microbiota. The role of dysbacteriosis in obesity, insulin resistance, diabetes and metabolic syndrome]. *Ory Hetil* 2016, 157(1):13-22.
14. Lopetuso L R, Chowdhry S, Pizarro T T: Opposing Functions of Classic and Novel IL-1 Family Members in Gut Health and Disease. *Front Immunol* 2013, 4:181.
15. Schlegel H: Allgemeine Mikrobiologie. *Georg Thieme Verlag* 1992.
16. Fox A D, Kripke S A, De Paula J, Berman J M, Settle R G, Rombeau J L: Effect of a glutamine-supplemented enteral diet on methotrexate-induced enterocolitis. JPEN J Parenter Enteral *Nutr* 1988, 12(4):325-331.
17. Roth E, Karner J, Ollenschlager G, Karner J, Simmel A, Furst P, Funovics J: Alanylglutamine reduces muscle loss of alanine and glutamine in post-operative anaesthetized dogs. *Clin Sci (Lond)* 1988, 75(6):641-648.
18. Guandalini S, Rubino A: Development of dipeptide transport in the intestinal mucosa of rabbits. *Pediatr Res* 1982, 16(2):99-103.
19. Miller P M, Burston D, Brueton M J, Matthews D M: Kinetics of uptake of L-leucine and glycylsarcosine into normal and protein malnourished young rat jejunum. *Pediatr Res* 1984, 18(6):504-508.
20. Vazquez J A, Morse E L, Adibi S A: Effect of starvation on amino acid and peptide transport and peptide hydrolysis in humans. *Am J Physiol* 1985, 249(5 Pt 1):G563-566.
21. Ladirat S E, Schols H A, Nauta A, Schoterman M H, Keijser B J, Montijn R C, Gruppen H, Schuren F H: High-throughput analysis of the impact of antibiotics on the human intestinal microbiota composition. *J Microbiol Methods* 2013, 92(3):387-397.
22. Minekus M, Smeets-Peeters M, Bernalier A, Marol-Bonnin S, Havenaar R, Marteau P, Alric M, Fonty G, Huis in't Veld J H: A computer-controlled system to simulate conditions of the large intestine with peristaltic mixing, water absorption and absorption of fermentation products. *Appl Microbiol Biotechnol* 1999, 53(1):108-114.
23. Scholz R, Molohon K J, Nachtigall J, Vater J, Markley A L, Sussmuth R D, Mitchell D A, Borriss R: Plantazolicin, a novel microcin B17/streptolysin S-like natural product from *Bacillus amyloliquefaciens* FZB42. *J Bacteriol* 2011, 193(1):215-224.
24. Kozich J J, Westcott S L, Baxter N T, Highlander S K, Schloss P D: Development of a dual-index sequencing strategy and curation pipeline for analyzing amplicon sequence data on the MiSeq Illumina sequencing platform. *Appl Environ Microbiol* 2013, 79(17):5112-5120.
25. Caporaso J G, Lauber C L, Costello E K, Berg-Lyons D, Gonzalez A, Stombaugh J, Knights D, Gajer P, Ravel J, Fierer N et al: Moving pictures of the human microbiome. *Genome Biol* 2011, 12(5):R50.
26. Schloss P D, Westcott S L, Ryabin T, Hall J R, Hartmann M, Hollister E B, Lesniewski R A, Oakley B B, Parks D H, Robinson C J et al: Introducing mothur: open-source, platform-independent, community-supported software for describing and comparing microbial communities. *Appl Environ Microbiol* 2009, 75(23):7537-7541.
27. Kong Y: Btrim: a fast, lightweight adapter and quality trimming program for next-generation sequencing technologies. *Genomics* 2011, 98(2):152-153.
28. Edgar R C, Haas B J, Clemente J C, Quince C, Knight R: UCHIME improves sensitivity and speed of chimera detection. *Bioinformatics* 2011, 27(16):2194-2200.
29. Wang Q, Garrity G M, Tiedje J M, Cole J R: Naive Bayesian classifier for rapid assignment of rRNA sequences into the new bacterial taxonomy. *Appl Environ Microbiol* 2007, 73(16):5261-5267.
30. Eren A M, Maignien L, Sul W J, Murphy L G, Grim S L, Morrison H G, Sogin M L: Oligotyping: Differentiating between closely related microbial taxa using 16S rRNA gene data. Methods Ecol Evol 2013, 4(12).

The invention claimed is:

1. A preparation, comprising:
   at least one probiotic strain selected from the group consisting of *Bacillus subtilis* DSM 32315 and *Bacillus amyloliquefaciens* CECT 5940; and
   a dipeptide comprising at least one selected from glycine-glutamine, alanine-glutamine, and glycine-glutamate,
   wherein a total amount of probiotic strain and dipeptide is at least 40 wt. %, of total preparation weight,
   wherein the probiotic strain is present in an amount of $1 \times 10^8$ and $2 \times 10^{10}$ CFU and the dipeptide is present in an amount of 50 mg and 800 mg of the dipeptide, and
   wherein when the preparation is consumed by a subject, the preparation increases n-butyrate production.

2. The preparation of claim 1, wherein the preparation comprises an enteric coating comprising a methyl acrylate-methacrylic acid copolymer, cellulose acetate phthalate, cellulose acetate succinate, hydroxypropyl methyl cellulose phthalate, hydroxypropyl methyl cellulose acetate succinate, polyvinyl acetate phthalate, methyl methacrylate-methacrylic acid copolymer, shellac, cellulose acetate trimellitate, sodium alginate, and/or zein.

3. A feed or food supplement, comprising the preparation of claim 1.

4. A synbiotic ingredient suitable for feed or a food product, comprising the preparation of claim 1.

5. A feed or foodstuff composition, comprising:
   the preparation of claim 1; and
   a further feed or food ingredient comprising a protein, carbohydrate, fat, further probiotic, prebiotic, enzyme, vitamin, immune modulator, milk replacer, mineral, amino acid, coccidiostat, acid-based product, and/or medicine.

6. A pharmaceutical composition, comprising:
   the preparation of claim 1; and
   a pharmaceutically acceptable carrier.

7. The composition of claim 5, wherein the composition prevents or treats diarrhea, constipation, irritable bowel syndrome, Crohn's disease, ulcerative colitis, colorectal cancer, bowel cancer, cardiovascular disease, arteriosclerosis, fatty liver disease, hyperlipidemia, hypercholesterolemia, obesity, adipositas, type 2 diabetes, metabolic syndrome, chronic inflammatory disease, or allergic disease.

8. A capsule, comprising:
   at least one probiotic strain selected from the group consisting of *Bacillus subtilis* DSM 32315 and *Bacillus amyloliquefaciens* CECT 5940; and
   a dipeptide comprising at least one selected from glycine-glutamine, alanine-glutamine, and glycine-glutamate,
   wherein the probiotic strain is present in an amount of $1 \times 10^8$ and $2 \times 10^{10}$ CFU and the dipeptide is present in an amount of 50 mg and 800 mg of the dipeptide,
   wherein the probiotic strain and dipeptide are present in an amount of at least 40 wt. % of total capsule filling weight, and
   wherein when the capsule is consumed by a subject, the capsule increases n-butyrate production.

9. The capsule of claim 8, further comprising:
   vitamin A as all-trans-retinol, all-trans-retinyl-ester(s), all-trans-beta-carotene, and/or other provitamin A carotenoid(s);
   vitamin B1 as thiamine;
   vitamin B2 as riboflavin;
   vitamin B3 as niacin;
   vitamin B5 as pantothenic acid;
   vitamin B6 as pyridoxine;
   vitamin B7 as biotin;
   vitamin B9 as folic acid or folate;
   vitamin B12 as cobalamin(s);
   vitamin C as ascorbic acid;
   vitamin D as calciferol(s);
   vitamin E as tocopherol(s) and/or tocotrienol(s); and/or
   vitamin K as quinone(s).

10. The capsule of claim 8, further comprising:
    sulfur, iron, chlorine, calcium, chromium, cobalt, copper, zinc, magnesium, manganese, molybdenum, iodine, and/or selenium.

11. The capsule of claim 8, further comprising:
an inulin, fructooligosaccharide, galactooligosaccharide, starch, pectin, beta-glucan, and/or xylooligosaccharides.

12. The capsule of claim 8, further comprising:
a plant extract, optionally from broccoli, olive fruit, pomegranate, blackcurrant, blueberry, bilberry, sea buckthorn, camu camu, boysenberry, curcuma, ginger, garlic, grape seeds, acai berry, aronia, goji berry, horseradish, boswellia serrata, spirulina, panax ginseng, cannabidiol, rose hip, pu erh, sencha, echinacea, and/or green tea leaves.

13. The capsule of claim 8, further comprising:
an enteric coating comprising a methyl acrylate-methacrylic acid copolymer, cellulose acetate phthalate, cellulose acetate succinate, hydroxypropyl methyl cellulose phthalate, hydroxypropyl methyl cellulose acetate succinate, polyvinyl acetate phthalate, methyl methacrylate-methacrylic acid copolymer, shellac, cellulose acetate trimellitate, sodium alginate, and/or zein.

14. A preparation, consisting of:
at least one probiotic strain selected from the group consisting of *Bacillus subtilis* DSM 32315 and *Bacillus amyloliquefaciens* CECT 5940; and
a dipeptide consisting of glycine-glutamine, alanine-glutamine, or glycine-glutamate,
wherein a total amount of probiotic strain and dipeptide is at least 40 wt. %, of total preparation weight,
wherein the probiotic strain is present in an amount of $1\times10^8$ and $2\times10^{10}$ CFU and the dipeptide is present in an amount of 50 mg and 800 mg of the dipeptide, and
wherein when the preparation is consumed by a subject, the preparation increases n-butyrate production.

15. A capsule, consisting of:
at least one probiotic strain selected from the group consisting of *Bacillus subtilis* DSM 32315 and *Bacillus amyloliquefaciens* CECT 5940; and
a dipeptide consisting of glycine-glutamine, alanine-glutamine, or glycine-glutamate,
wherein the probiotic strain is present in an amount of $1\times10^8$ and $2\times10^{10}$ CFU and the dipeptide is present in an amount of 50 mg and 800 mg of the dipeptide,
wherein the probiotic strain and dipeptide are present in an amount of at least 40 wt. % of total capsule filling weight, and
wherein when the capsule is consumed by a subject, the capsule increases n-butyrate production.

\* \* \* \* \*